United States Patent [19]

Nishimura et al.

[11] Patent Number: 5,120,841
[45] Date of Patent: Jun. 9, 1992

[54] CEPHALOSPORIN ESTER DERIVATIVES

[75] Inventors: Tatsuo Nishimura, Toyonaka; Yoshinobu Yoshimura, Ibaraki; Mitsuo Numata, Takatsuki, all of Japan

[73] Assignee: Takeda Chemical Industries, Ltd., Osaka, Japan

[21] Appl. No.: 27,433

[22] Filed: Mar. 18, 1987

Related U.S. Application Data

[63] Continuation of Ser. No. 616,259, Jun. 1, 1984.

[30] Foreign Application Priority Data

Jun. 2, 1983 [JP] Japan ................................. 58-99212
Apr. 16, 1984 [JP] Japan ................................. 59-76834

[51] Int. Cl.⁵ ............... C07D 501/36; A61K 31/545
[52] U.S. Cl. ................................................ 540/227
[58] Field of Search ..................... 540/227; 514/206

[56] References Cited

U.S. PATENT DOCUMENTS

| 3,935,204 | 1/1976 | Dahlen et al. | 540/226 X |
| 4,080,498 | 3/1978 | Numata et al. | 540/227 |
| 4,189,479 | 2/1980 | Kakeya et al. | 540/227 |
| 4,344,968 | 8/1982 | Aoda et al. | 424/81 |
| 4,483,855 | 11/1984 | Nakao et al. | 540/228 |
| 4,497,809 | 2/1985 | Yoshimwa et al. | 514/206 |
| 4,616,008 | 10/1986 | Hirai et al. | 514/200 |

FOREIGN PATENT DOCUMENTS 109294 5/1984 European Pat. Off. ............ 540/227

OTHER PUBLICATIONS

Takeda, Chem. Abstracts 97 (1982), entry 144673x.

Primary Examiner—Nicholas S. Rizzo
Attorney, Agent, or Firm—Antonelli, Terry, Stout & Kraus

[57] ABSTRACT

A compound of the formula:

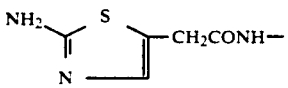

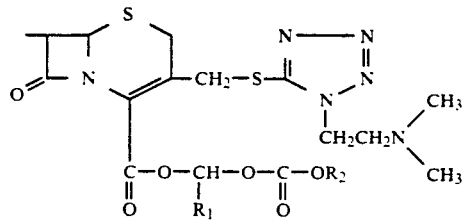

wherein $R_1$ is a hydrogen atom or a lower alkyl group; $R_2$ is an unsubstituted or lower alkyl-substituted alicyclic alkyl group of 3 to 12 carbon atoms or a $C_{3-6}$ alicyclic alkyl-substituted lower alkyl group or a pharmaceutically acceptable salt thereof, processes for preparing the same, a pharmaceutical composition thereof are provided. The compound has an improved absorbability and can be orally applied as antibiotics.

5 Claims, No Drawings

CEPHALOSPORIN ESTER DERIVATIVES

This is a continuation of application Ser. No. 616,259, filed Jun. 1, 1984.

This invention relates to compounds of the formula:

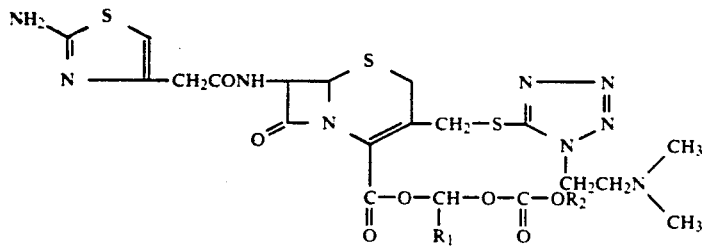

(wherein $R_1$ is a hydrogen atom or a lower alkyl group; and $R_2$ is an unsubstituted or lower alkyl-substituted alicyclic alkyl group of 3 to 12 carbon atoms or a $C_{3-6}$ alicyclic alkyl-substituted lower alkyl group) and pharmaceutically acceptable salts thereof.

For promoting the absorption, on oral administration, of the non-ester form of compound (I), i.e. 7β-[2-(2-aminothiazol-4-yl) acetamido]-3-[[[1-(2-dimethylaminoethyl)-1H-tetrazol-5-yl]thio]methyl]-ceph-3-em-4-carboxylic acid (common name: cefotiam, hereinafter referred to briefly as compound (II)) described in U.S. Pat. No. 4080498), it has been suggested to convert the compound (II) into a straight-chain or branched $C_{1-5}$ alkoxy-carbonyloxyalkyl ester thereof for instance (e.g. U.S. Pat. No. 4189479 and Japanese published unexamined patent application No. 77690/1982).

However, these esters have still much to be desired in the respects of absorbability and stability, etc.

The present inventors conducted an intensive study of various ester derivatives of the compound (II) and found that the compound (I) or a salt thereof is efficiently absorbed from the gastrointestinal tract and, after absorption, quickly transferred into the blood stream in the form of non-ester compound (II) to establish a high blood level of the compound (II) so that it is of value as an orally administrable broad-spectrum antibiotic displaying potent inhibitory effects not only against gram-positive and gram-negative bacteria but also against resistant strains thereof. We have also found that, by conversion of the compound (I) into a salt thereof, water-solubility and absorption efficiency of the compound (I) are much increased and at the same time isolation stability and formulation of the compound (I) become much easier. Based on these findings, the present invention has been accomplished.

Referring to the above formula (I), the lower alkyl group represented by $R_1$, the substituent lower alkyl group in the lower alkyl-substituted $C_{3-12}$ alicyclic alkyl group represented by $R_2$ and the lower alkyl group in the $C_{3-6}$ alicyclic alkyl-substituted lower alkyl group represented by $R_2$ are respectively a straight-chain or branched lower alkyl group of 1 to 3 carbon atoms such as methyl, ethyl, propyl, isopropyl, etc. The $C_{3-12}$ alicyclic alkyl group in the lower alkyl-substituted $C_{3-12}$ alicyclic alkyl group represented by $R_2$ is a saturated unbridged (monocyclic)alicyclic alkyl group of 3 to 12 carbon atoms, such as cyclopropyl, cyclobutyl, cyclopentyl, cyclohexyl, cycloheptyl, cyclooctyl, cyclononyl, cyclodecyl, cycloundecyl, cyclododecyl, etc., or a bridged alicyclic alkyl group of 4 to 12 carbon atoms, such as bicyclo[2,2,1]heptyl, bicyclo[3,2,1]octyl, bicyclo[3,3,1]nonyl, tricyclo[3,3,2,1,$^{3,6}$]undecyl, adamantyl, etc. The substituent $C_{3-6}$ alicyclic alkyl group in the $C_{3-6}$ alicyclic alkyl-substituted lower alkyl group $R_2$ is a saturated unbridged monocyclic alicyclic alkyl group of 3 to 6 carbon atoms such as cyclopropyl, cyclobutyl, cyclopentyl, cyclohexyl, etc.

The substituent lower alkyl group in the lower alkyl-substituted $C_{3-12}$ alicyclic alkyl group represented by $R_2$ may be present in the number of 1 or 2.

Preferably, $R_1$ is a straight-chain or branched lower alkyl group of 1 to 3 carbon atoms, and $R_2$ is a saturated unbridged (monocyclic) alicyclic alkyl group of 3 to 12 carbon atoms which may be substituted with one or two straight-chain or branched lower alkyl groups of 1 to 3 carbon atoms.

More preferably, $R_2$ is cyclopentyl, cyclohexyl, 2-methylcyclohexyl, 3-methylcyclohexyl, cycloheptyl, cyclododecyl or 5-methyl-2-(1-methylethyl)cyclohexyl.

Since the compound (I) is basic in itself, it can be converted into an acid addition salt thereof. Generally, 1 mole of the compound (I) forms an acid addition salt with 1 or 2 moles of an acid. Acids which are preferably employed for the formation of such acid addition salts include those known to form pharmaceutically acceptable salts with pencillins and cephalosporins; for example, inorganic acids such as hydrochloric acid, sulfuric acid, phosphoric acid, etc. and organic acids such as maleic acid, acetic acid, citric acid, succinic acid, tartaric acid, malic acid, malonic acid, fumaric acid, benzoic acid, mandelic acid, ascorbic acid, methanesulfonic acid, etc. Preferred salts of the compound (I) are the monohydrochloride and dihydrochloride. The most desirable is the dihydrochloride. The aminothiazole group of the compound (I) or a salt thereof may exist in the form of its tautomer i.e. iminothiazoline. As the compound (I) or a salt thereof has an asymmetric carbon in the carboxyl ester group at 4-position of the cephem nucleus, there exist two optically active forms (D-isomer and L-isomer). The compound (I) or a salt. thereof can generally be used as a racemic compound but either the D-isomer or L-isomer or a mixture of such optical isomers can also be employed. The compound (I) or a salt thereof is absorbed well through the gastrointestinal tract and after absorption the ester moiety at its 4-carboxyl position is promptly hydrolyzed with enzyme in the body to give the non-ester form of the compound (I), which is the compound (II).

The compound (II) has strong antibacterial activity as mentioned in Antimicrobial Agent and Chemotherapy 14, 557–568 (1978). Thus, the compound (II) displays potent antibacterial activity against gram-positive bacteria such as *Staphylococcus aureus*, etc. and gram-negative bacteria such as *Escherichia coli, Klebsiella*

*pneumoniae, Proteus vulgaris, Proteus mirabilis* and *proteus morganii*.

Since the compound (I) or a salt thereof, when administered by the oral route, gives a high concentration of the compound (II) in the blood, it is effective in the treatment of infections due to said bacteria in man and other mammalian animals, such as respiratory tract and urinary tract infections due to said bacteria.

The compound (I) or a salt thereof is low in toxicity ($LD_{50} \geq 3$ g/kg, mice, p.o.) and can be orally administered. Therefore, in combination with per se known pharmaceutically acceptable excipients (e.g. starch, lactose, calcium carbonate, calcium phosphate, etc.), binders (e.g. starch, gum arabic, carboxymethylcellulose, hydroxypropylcellulose, crystalline cellulose, etc.), lubricants (e.g. magnesium stearate, talc, etc.) or/and disintegrating agents (e.g. carboxymethylcalcium, talc, etc.), the compound (I) or a salt thereof can be formulated into such dosage forms as capsules, powders, fine granules, granules, tablets, etc. It is also possible to add about 1 to 5 mole equivalents of a solid organic acid (e.g. citric acid, malic acid, tartaric acid, succinic acid, ascorbic acid, mandelic acid, etc.) to the compound (I) or a salt thereof and mold the mixture into granules in the conventional manner. Such granules can be further processed into capsules, tablets, etc. by established pharmaceutical procedures.

With regard to the dosage regimen, the compound (I) or a salt thereof can be administered at a daily dose of 0.3 to 5 g per adult human, preferably 0.5 to 3 g per adult human, divided into 3 or 4 equal doses.

The compound (I) or a salt thereof can be produced by per se known processes (for example, the processes described in the specifications of U.S. Pat. No. 4080498, U.S. Pat. No. 4189479 and Japanese published unexamined patent application No. 77690/1982). Moreover, the compound (I) or a salt thereof can be produced by esterifying the compound (II) or a salt thereof with a compound of the formula

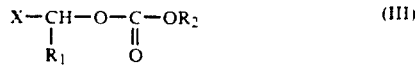

(wherein X is a halogen atom; $R_1$ and $R_2$ have the same meaning as defined hereinbefore).

Referring to the above formula (III), the halogen atom represented by X is for example chlorine, bromine and iodine. Of these species, X is preferably iodine for the purpose of esterification.

As the compound (III) has an asymmetric carbon atom, it can be optically resolved into D- and L-isomers by a per se known procedure and either of the isomers or a mixture thereof can be used in the contemplated esterification reaction. The starting compound (II) can be subjected to the reaction in the form of an acid addition salt with an inorganic acid such as hydrochloric acid, sulfuric acid and nitric acid, or an organic acid such as oxalic acid and p-toluenesulfonic acid, or in the form of a salt with a base such as an alkali metal, e.g. sodium, potassium, etc., an alkaline earth metal, e.g. calcium, magnesium, etc., and an organic amine, e.g. triethylamine, trimethylamine, pyridine, collidine, lutidine, etc.

In conducting the esterification reaction, the starting compound (III) is used in a proportion of about 1 to 10 mole equivalents to each equivalent of the starting compound (II) or a salt thereof.

This reaction is generally carried out in a solvent inert to the reaction. Suitable species of such solvent include amides such as N,N-dimethylformamide (hereinafter referred to briefly as DMF), N,N-dimethylacetamide (hereinafter referred to briefly as DMAC), hexamethylphosphorotriamide (hereinafter referred to briefly as HMPA), etc., halogenated hydrocarbons such as dichloromethane, chloroform, etc., sulfoxides such as dimethyl sulfoxide (hereinafter referred to briefly as DMSO), sulfonate, etc., ethers such as dioxane, tetrahydrofuran (hereinafter referred to briefly as THF), ketones such as acetone, methyl ethyl ketone, etc., nitriles such as acetonitrile, etc., liquefied sulfur dioxide, and so forth. Preferred are DMF, DMAC, HMPA, acetone, acetonitrile, liquefied sulfur dioxide, etc. This esterification reaction is conducted generally at a temperature between about $-20°$ C. and $20°$ C. While the reaction can be conducted in the absence of a catalyst, a catalyst such as a phase transfer catalyst (e.g. 18-crown-6, etc.) can be employed. When liquefied sulfur dioxide is used as the solvent, the reaction is preferably conducted at a temperature near the boiling point ($-10°$ C.) of the solvent, i.e. $-10°$ C. to $-20°$ C. The reaction time is generally several minutes to about 1 hour, depending on the species of reactants and solvent, etc.

The compound (I) or a salt thereof can also be produced by the following processes. Thus, a compound of the formula:

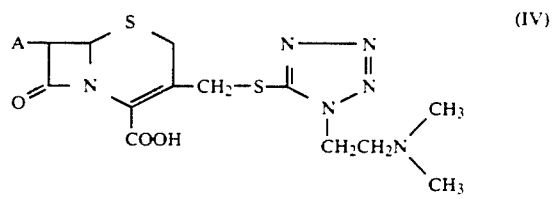

(wherein A is an amino group or an acylamino group other than 2-(2-aminothiazol-4-yl)acetylamino) or a salt thereof is reacted with the compound (III) in the same manner as the above-described esterification reaction and when A is an acylamino group, the resulting ester is reacted with phosphorus pentachloride and, then, with alcohol (e.g. methanol, ethanol, propanol, isopropanol, n-butanol, etc.) (the process described in Journal of Medicinal Chemistry 18, 992 (1975), and West German Laid-open Patent Application Nos. 2460331 and 2460332). The resulting compound of the formula:

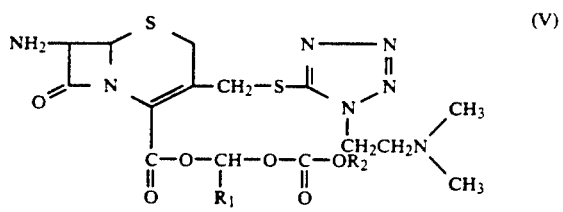

(wherein symbols have the same meanings as defined hereinbefore) or a salt thereof is acylated with 2-(2-aminothiazol-4-yl)acetic acid of the formula:

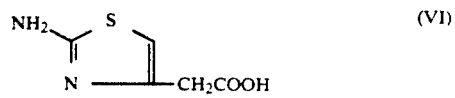

or its reacted derivative, to give the compound (I) or a salt thereof.

Referring to the above formula (IV), when A is an acylamino group, the acyl group can be any of the acyl groups known per se in the field of cephalosporin compounds. Preferred species of such acylamino group are e.g. acetylamino, benzoylamino, phenylacetylamino, thienylacetylamino, phenyloxyacetylamino, and 5-amino-5-carboxyvalerylamino (the substituent amino group may be protected with phthaloyl or the like). When A is an amino group or an amino-substituted acylamino group, the substituent amino group is preferably protected before the reaction and the protective group therefor may, for example, be per se known protective groups for an amino group, such as t-butoxycarbonyl, carboxybenzyloxy, 2-hydroxy-1-napthocarbonyl, trichloroethoxycarbonyl, 2-ethoxycarbonyl-1-methylvinyl, or 2-methoxycarbonyl-1-methylvinyl.

The deacylation of the ester compound produced by reacting the compound (IV) (when A is an acylamino group) with the compound (III) is conducted in a per se known manner, using generally about 2 to 5 mole equivalents of phosphorus pentachloride and about 10 to 40 mole equivalents of alcohol per mole of the starting ester compound. This reaction is generally conducted in an inert solvent such as halogenated hydrocarbons, e.g. dichloromethane, chloroform, etc. For the purpose of accelerating the reaction, a tertiary amine such as triethylamine, pyridine, N,N-dimethylaniline may be added to the reaction system. The reaction temperature is about $-40°$ C. to about $-20°$ C. The reaction time is usually about 1 hour.

When the resulting compound (V) or a salt thereof is reacted with the compound (VI), that is 2-(2-aminothiazol-4-yl)acetic acid, or its reactive derivative to produce the compound (I) or a salt thereof, the amino group of the compound (VI) is preferably protected beforehand and the protective group can be similar to the protective group for the amino group of the compound (IV). In this reaction, the compound (VI) may be used in the form of its reactive derivative. Thus, for example, it is subjected to said acylation reaction in the form of the corresponding acid halides, acid anhydrides, mixed acid anhydrides, active amides, active esters, etc. Preferred are the active esters, mixed acid anhydrides, acid halides etc. Examples of such active esters are p-nitrophenyl ester, 2-4-dinitrophenyl ester, pentachlorophenyl ester, N-hydroxyphthalimide ester, and the ester formed by means of a Vilsmeier or similar reagent, and so on. The mixed acid anhydrides are those prepared from carbonic monoesters such as monomethyl carbonate, monoisobutyl carbonate, etc., and those prepared from alkanoic acids of 2 to 5 carbon atoms which may be substituted by halogens, such as pivalic acid, trichloroacetic acid, etc. Examples of such acid halides are acid chloride, acid bromide, etc. In this reaction, the compound (VI) or its reactive derivative is used in a proportion of about 1 to 2 mole equivalents to each mole equivalent of the compound (V) or a salt thereof.

When the compound (VI) is used in the form of free acid or a salt thereof, a suitable condensing agent is employed. Examples of such suitable condensing agent include N,N′di-substituted carbodiimides such as N,N′-dicyclohexylcarbodiimide, azolides such as N,N′-carbonylimidazole, N,N′-thionyldiimidazole, etc., and such dehydrating agents as N-ethoxycarbonyl-2-ethoxy-1,2-dihydroquinoline, phosphorus oxychloride, alkoxyacetylenes (e.g. ethoxyacetylene) and so on. When such a condensing agent ss employed, the reaction appears to proceed via formation of a reactive derivative of the carboxylic acid.

Generally this reaction can be smoothly conducted in a solvent. Examples of the solvent include the common solvents which do not interfere with the contemplated reaction, such as water, acetone, diisobutyl ketone, THF, ethyl acetate, dioxane, acetonitrile, chloroform, dichloromethane, dichloroethylene, pyridine, dimethylaniline, DMF, DMAC, DMSO, etc., as well as mixtures of such solvents. While the reaction temperature is virtually optional, the reaction is generally conducted under cooling or at room temperature. When the reaction proceeds with liberation of an acid, a base is added to the reaction system as necessary. The base used for this purpose is exemplified by aliphatic, aromatic or heterocyclic nitrogen-containing bases such as triethylamine, N,N-dimethylaniline, N-ethylmorpholine, pyridine, collidine, 2,6-lutidine, etc., alkali metal carbonates such as sodium carbonate, potassium carbonate etc., and alkali metal bicarbonates such as potassium hydrogen carbonate, sodium hydrogen carbonate, etc. When the acylation reaction proceeds dehydratingly, it is preferable to remove water from the solvent. In some instances, the reaction is conducted under moisture-free conditions, e.g. in an inert gaseous atmosphere such as nitrogen gas. When the reaction product has a protective group, the protective group is removed by a per se known procedure.

The compound (I) or a salt thereof can also be produced by the following procedure. Thus, the compound (V) is reacted with a 4-halo-3-oxobutyryl halide, which is obtained by reacting diketene with a halogen (e.g. chlorine or bromine) in an equimolar ratio, to give a compound of the formula:

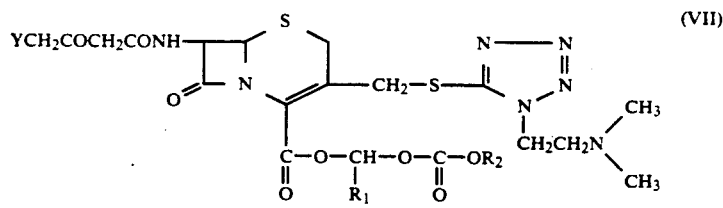
(VII)

(wherein Y is a halogen atom; $R_1$ and $R_2$ have the same meanings as defined hereinbefore), which is then reacted with thiourea. In the above formula (VII), the halogen atom Y is for example chlorine and bromine.

In reaction of the compound (VII) with thiourea, this urea is preferably used as it is but may be used in the form of a salt with an alkali metal such as lithium, sodium and potassium, or ammonium salt. Generally the reaction is carried out using the two reactants in an equimolar ratio in a solvent and, in some instances, can be conducted in the presence of 1 to 2 molar equivalents of a base if necessary. Preferred examples of said solvent include water, methanol, ethanol, acetone, dioxane, acetonitrile, chloroform, ethylene chloride, THF, ethyl acetate, DMF, DMAC, DMSO, etc. Among these solvents, hydrophilic solvents can be used in admixture with water. Preferred examples of said base include alkali metal hydroxides such as sodium hydroxide, potassium hydroxide, etc., alkali metal carbonates such as sodium carbonate, potassium carbonate, etc., alkali metal hydrogen carbonates such as sodium hydrogen carbonate, etc., and organic tertiary amines such as triethylamine, trimethylamine, pyridine, etc. While there is virtually no limitation on the reaction temperature, generally the reaction is preferably conducted under cooling. The reaction generally proceeds at a fast rate and goes to completion within 10 minutes, although a reaction time in excess of 30 minutes is at times required. The compound (VII) can be easily produced by the above-described process or other processes known per se.

The compound (I) or a salt thereof can also be produced by reacting a compound of the formula:

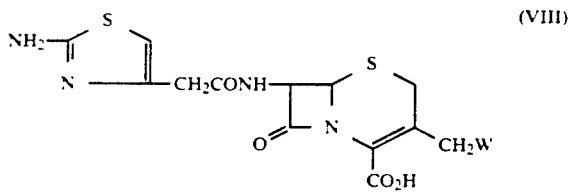

(wherein W is acetoxy, acetoacetoxy, a halogen atom or a carbamoyloxy) or a salt thereof with the compound (III) in the same manner as the esterification reaction described hereinbefore and reacting the resulting compound of the formula:

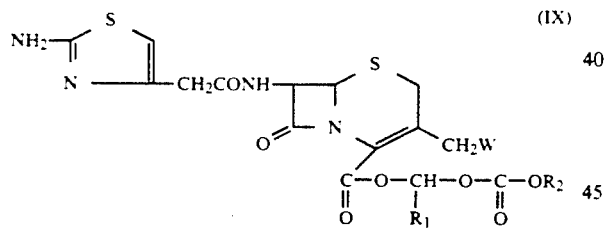

(wherein symbols have the same meanings as defined hereinbefore) or a salt thereof with 1-(2-dimethylaminoethyl)-5-mercapto-1H-tetrazole. Referring to the above formulas (VIII) and (IX), the halogen atom represented by W is, for example, chlorine, bromine and iodine In this reaction, the starting material 1-(2-dimethylaminoethyl)-5-mercapto-1H-tetrazole is used in an approximately equimolar proportion with respect to the compound (IX) or a salt thereof.

This reaction can generally be conducted smoothly in a solvent. Examples of such solvent include water, THF, ethyl acetate, dioxane, acetonitrile, chloroform, dichloromethane, DMF, DMAC, DMSO, etc. When water is used, it can be used in admixture with a highly water-miscible solvent. Generally, this reaction is conducted in the presence of a base. Preferred examples of the base are weak bases such as alkali metal carbonates (e.g. sodium carbonate, potassium carbonate etc.), alkali metal bicarbonates (e.g. sodium hydrogen carbonate, potassium hydrogen carbonate, etc.). The base is used in an approximately equimolar proportion with respect to the starting compound, 1-(2-dimethylaminoethyl)-5-mercapto-1H-tetrazole. While the reaction temperature is more or less optional, the reaction is generally conducted at room temperature up to 40° through 60° C. The reaction time is about 30 minutes to about 3 hours, depending on the species of solvent and the reaction temperature.

If the compound (I) or a salt thereof prepared as above contains its $\Delta^2$-isomer, the isomer can be converted to the compound (I) or a salt thereof by, for example, isomerizing the isomer to the $\Delta^3$-isomer by a per se known method (Journal of Medicinal Chemistry, Vol. 18, 986 (1975)), or converting the isomer to the $\Delta^3$-isomer via a corresponding S-oxide derivative and reducing it.

When the compound (I) is produced in the form of free base, it can be converted to a salt thereof by dissolving it in an inert solvent such as dichloromethane and chloroform, and adding about 1 to 10 mole equivalents of an acid to the solution.

When the compound (I) is produced in the form of an acid addition salt, it can be converted to the form of free base according to a per se known procedure.

When the compound (I) or a salt thereof is produced in the form of a racemic mixture, it can be subjected to the optical resolution according to a per se known procedure to isolate the optically active compounds (D- and L-isomers). The resulting compound (I) or a salt thereof can be isolated and purified by per se known procedures such as solvent extraction, pH adjustment, solvent transformation, crystallization, recrystallization and chromatography.

The starting compound (III) is produced by per se known processes (for example, the process described in Great Britain Patent 1426717). The compound (III) can also be produced by the process illustrated below:

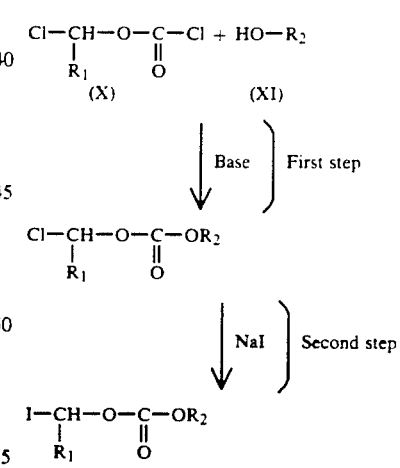

(In the above formulas, $R_1$ and $R_2$ have the same meanings as defined hereinbefore.)

Chloroformate (X), which is the starting compound in the first step of the reaction in the above equations, is produced by per se known process (for example, EP-40153 A). Further, the compound (X) is produced by reacting an aldehyde of the formula $R_1CHO$ (wherein $R_1$ has the same meaning as defined above) with phosgene in the presence of a catalyst (phosgenation), As the catalysts used here, there are, for example, tertiary amines such as N,N-dimethylaniline, N,N-dimethylaminopyridine and pyridine; aromatic monoamines such as imidazole; substituted amides such as DMF; lower tetraalkylureas (1-4 carbon atoms) or thioureas such as tetrabutylurea, tetramethylurea, tetrabutylthiourea and tetramethylthiourea; aliphatic tertiary phosphines such as trioctylphosphine; and substituted phosphoroamides such as HMPA. The aldehyde which is the starting compound is used in an approximately equimolar ratio to phosgene. The catalyst can be used in 0.01-0.1 mole equivalent to the starting material aldehyde.

The phosgenation is usually conducted in a solvent inactive to the reaction. Suitable solvents are halogenated hydrocarbons such as carbon tetrachloride, chloroform and methylene chloride; aromatic hydrocarbons such as toluene and benzene; and aliphatic hydrocarbons such as hexane.

The phosgenation is usually conducted under atmospheric pressure; however, when the starting material aldehyde is volatile, the reaction may be conducted under a pressure a little higher than the atmospheric pressure.

Reaction temperature varies depending upon the species of catalyst and the amount thereof used, but it is from approximately $-40°$ C. to $100°$ C. Reaction time is about 30 minutes to 5 hours.

The compound (X) produced after the completion of this phosgenation can be isolated and purified by condensation, distillation, etc. under atmospheric pressure or reduced pressure.

The compound of formula (III) wherein X is iodine, i.e. iodoalkyl carbonate, is produced by reacting the compound (X) with the compound (XI) in the presence of a base (the reaction of the first step) and reacting the resulting reaction product (the compound (III) wherein X is chlorine) with sodium iodine (the reaction of the second step).

In the first step of reaction, the starting compounds (X) and (XI) are used in an approximately equimolar ratio. This reaction is generally conducted in a solvent. Suitable species of the solvent are such inert solvents as dichloromethane, chloroform, diethyl ether, ethyl acetate, etc. The base used for this reaction may be an organic tertiary amine such as pyridine; lutidine, triethylamine, diisopropylethylamine, etc. The base is used in an approximately equimolar amount relative to the compound (X). This reaction proceeds at a temperature of $-80°$ C. to $40°$ C. While the reaction time varies with the reaction temperature, for instance, it is generally about 30 minutes to a few days.

Following the above first step of reaction, the reaction mixture is subjected to washing with water, extraction, concentration, distillation, column chromatography or/and the like, and the resulting chloroalkyl carbonate is reacted with sodium iodide to give iodoalkyl carbonate (the reaction of the second step).

The amount of sodium iodide used in the above second step of reaction is about 1 to about 10 mole equivalents with respect to chloroalkyl carbonate. This second-step reaction is conducted in the presence of common solvent such as acetone, acetonitrile, DMF, DMSO, etc.

The reaction proceeds in the neighborhood of room temperature to about $70°$ C. The reaction time is generally about 15 minutes to about 24 hours.

The reaction product can be isolated and purified by per se known procedures such as solvent extraction, pH adjustment, distillation, distillation under reduced pressure, solvent transformation, chromatography, etc.

The compound (X) is produced in the form of a racemic mixture according to the method mentioned above or an analogous method thereto.

When the compound (X) in the form of a racemic mixture is subjected to the following reaction, the resulting compound (III) (wherein X is chlorine or iodine) is also produced in the form of racemic mixture.

The following Reference Examples, Examples, Formulation Examples and Experimental Example are further illustrative in further detail but by no means limitative of the invention.

The symbols used in these Reference Examples and Examples have the meanings defined below.

s: singlet; b: broad; d: doublet; d.d: double-doublet; t: triplet; q: quartet; ABq: AB-pattern quartet; m: multiplet; quin: quintet; TMS: tetramethylsilane.

Unless otherwise indicated, NMR (nuclear magnetic resonance) spectra were measured by means of a Varian XL-100A (100 MHz, Varian associates; U.S.A.) spectrometer.

REFERENCE EXAMPLE 1-1

Chloromethyl Cyclohexyl Carbonate

A solution of 3.0 g of cyclohexanol and 2.4 ml of pyridine in 30 ml of methylene chloride is cooled to $-78°$ C. and, with stirring, 2.4 ml of chloromethyl chloroformate is added dropwise to the solution. After completion of addition, a cold bath is removed. The mixture is stirred at room temperature for 16 hours, washed with three 30-ml portions of saturated aqueous sodium chloride and dried over anhydrous magnesium sulfate. The solvent is then distilled off under reduced pressure to give 4.5 g of colorless oil, which is crystallized from ligroine giving the title compound as colorless crystals melting at $36°-37°$ C.

IR (liquid film) cm$^{-1}$: 1760, 1450, 1380, 1360, 1250.
NMR (CDCl$_3$) δ: 0.7-2.3 (10H, m,

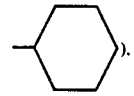

4.70 (1H, m,

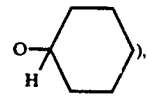

5.70 (2H, s, ClCH$_2$O).

Elemental analysis for C$_8$H$_{13}$O$_3$Cl: Calcd. (%): C, 49.37; H, 6.83. Found (%): C, 50.04; H, 6.70.

REFERENCE EXAMPLES 1-2 TO 1-8

The compounds obtained according to the same procedure as Reference Example 1-1 are listed in Table 1 together with their physico-chemical constants.

TABLE 1

Formula $$ClCH_2O-\underset{\underset{O}{\|}}{C}-O-R$$

| Reference Example No | R | IR(liquid film) (cm$^{-1}$) |
|---|---|---|
| 1-2 | (cyclopentyl) | 1760, 1450, 1370, 1350, 1260 |
| 1-3 | (cycloheptyl) | 1760, 1460, 1450, 1350, 1260 |
| 1-4 | (cyclooctyl) | 1760, 1480, 1450, 1350, 1260 |
| 1-5 | (cyclododecyl) | 1765, 1475, 1450, 1350, 1260 |
| 1-6 | (l-mentyl) | 1760, 1450, 1395, 1365, 1345, 1250 |
| 1-7 | (3-bornyl) | 1770, 1465, 1380, 1305, 1260 |
| 1-8 | (adamantyl) | 1765, 1455, 1445, 1360, 1355, 1250, 1220 |

REFERENCE EXAMPLE 2-1

1-Chloroethyl Cyclohexyl Carbonate

A solution of 1.83 g of cyclohexanol and 1.45 g of pyridine in 30 ml of methylene chloride is cooled to −78° C. and, with stirring, 2.0 ml of 1-chloroethyl chloroformate is added dropwise to the solution over a period of 10 minutes. After completion of addition, the cold bath is removed. The mixture is stirred at room temperature for 16 hours, washed with three 30-ml portions of saturated aqueous sodium chloride and dried over anhydrous magnesium sulfate. The solvent is then distilled off under reduced pressure to give 3.31 g (yield 88%) of the title compound as colorless oil.

bp 100°-113° C./5-6 mmHg.

IR$(_{film}{}^{liquid})$ cm$^{-1}$: 1760, 1455, 1390, 1360, 1260.

NMR (CDCl$_3$)δ: 1.0-2.3 (10H, m, 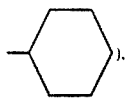), 1.83 (3H, d, J=6 Hz, CH$_3$), 4.68 (1H, m, 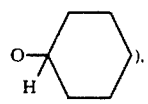), 6.40 (1H, q, J=6H, 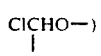

ClCHO—)

Elemental analysis for C$_9$H$_{15}$ClO$_3$: Calcd.(%): C, 52.30; H, 7.32. Found (%): C, 52.26; H, 7.32.

REFERENCE EXAMPLES 2-2 TO 2-21

The compounds obtained according to the same procedure as Reference Example 2-1 are listed in Table 2 together with their physico-chemical constants.

TABLE 2

Formula $$Cl-\underset{\underset{CH_3}{|}}{CH}-O-\underset{\underset{O}{\|}}{C}-O-R$$

| Reference Example No. | R | IR(liquid film) (cm$^{-1}$) |
|---|---|---|
| 2-2 | (cyclobutyl) | 1760, 1450, 1390, 1375, 1350, 1280, 1260 |
| 2-3 | (cyclopentyl) | 1760, 1440, 1375, 1350, 1325, 1260 |
| 2-4 | (cycloheptyl) | 1760, 1465, 1450, 1390, 1355, 1260 |
| 2-5 | —CH$_2$— (cyclopropylmethyl) | 1765, 1470, 1450, 1420, 1395, 1360, 1280, 1250, 1200 |
| 2-6 | —CH$_2$— (cyclopentylmethyl) | 1765, 1460, 1390, 1360, 1250 |

TABLE 2-continued

Formula $$Cl-CH(CH_3)-O-C(=O)-O-R$$

| Reference Example No. | R | IR(liquid film) (cm$^{-1}$) |
|---|---|---|
| 2-7 | —CH$_2$—(cyclohexyl) (cyclohexylmethyl) | 1765, 1455, 1390, 1350, 1260 |
| 2-8 | —CH$_2$CH$_2$—(cyclohexyl) (2-cyclohexylethyl) | 1765, 1455, 1395, 1355, 1260 |
| 2-9 | (4-methylcyclohexyl) | 1760, 1460, 1390, 1370, 1350, 1325, 1260 |
| 2-10 | (3-methylcyclohexyl) | 1760, 1460, 1380, 1365, 1355, 1320, 1260, 1220 |
| 2-11 | (2-methylcyclohexyl) | 1760, 1460, 1390, 1375, 1360, 1260, 1220 |
| 2-12 | ((cis)-2-methylcyclohexyl) | 1760, 1450, 1390, 1375, 1355, 1260, 1220 |
| 2-13 | ((trans)-2-methylcyclohexyl) | 1760, 1450, 1390, 1370, 1355, 1320, 1250, 1220 |
| 2-14 | ((endo)-3-norbornyl) | 1760, 1480, 1450, 1380, 1355, 1320, 1310, 1260 |
| 2-15 | ((exo)-2-norbornyl) | 1765, 1460, 1445, 1380, 1350, 1320, 1260, 1215 |
| 2-16 | (fenchyl) | 1760, 1465, 1400, 1380, 1355, 1320, 1280, 1260 |
| 2-17 | (l-menthyl) | 1760, 1460, 1395, 1375, 1355, 1260 |
| 2-18 | (2,6-dimethylcyclohexyl) | 1765, 1450, 1390, 1360, 1350, 1260 |
| 2-19 | (1-cyclohexylethyl) | 1760, 1455, 1390, 1360, 1260 |
| 2-20 | (2-ethylcyclohexyl) CH$_2$CH$_3$ | 1770, 1750, 1530, 1450, 1375, 1320, 1250, 1200 |
| 2-21 | (3,3,5-trimethylcyclohexyl) | 1760, 1465, 1385, 1370, 1315, 1260, 1240 |

REFERENCE EXAMPLE 3-1

1-Chloroproply Cyclopentylcarbonate

A solution of 1.37 g of cyclopentanol and 1.26 g of pyridine in 50 ml of methylene chloride is cooled to −78° C. and 2.50 g of 1-chloropropyl chloroformate is added dropwise while stirring over 10 minutes.

After adding dropwise, the cooling bath is taken off. The mixture is stirred at room temperature for 16 hours, and then washed 3 times with 100 ml of saturated sodium chloride aqueous solution.

After the mixture is dried over anhydrous magnesium sulfate and the solvent is distilled off under reduced pressure to give 3.11 g of the title compound as a colorless oily material.

IR(liquid film) cm$^{-1}$: 1760, 1460, 1440, 1375, 1325, 1260.

NMR (CDCl$_3$)δ: 1.05( 3H, t, J=7 Hz), 1.3-2.1(8H, m), 2.09(2H, quin, J=6 Hz), 5.18(1H, b), b 6.23(1H, t, J=5 Hz).

REFERENCE EXAMPLES 3-2-3-14

The compounds obtained according to the same procedure as Reference Example 3-1 are listed below in Table 3 together with their physico-chemical constants.

TABLE 3

Formula:

$$Cl-\underset{R_1}{CH}-O-\underset{\underset{O}{\|}}{C}-O-R_2$$

| Reference Example No. | R$_1$ | R$_2$ | IR(liquid film) (cm$^{-1}$) | NMR (CDCl$_3$, δ-value) Varian EM-360 (60 MHz) |
|---|---|---|---|---|
| 3-2 | —C$_2$H$_5$ | (cyclohexyl) | 1760, 1455, 1380, 1360, 1340, 1320, 1250 | 1.09(3H, t, J=7Hz), 1.0-2.3(10H, m), 2.08(2H, quin, J=6Hz), 4.70(1H, b), 6.24(1H, t, J=5Hz) |
| 3-3 | —C$_2$H$_5$ | (cycloheptyl) | 1760, 1465, 1390, 1360, 1340, 1320, 1260 | 1.05(3H, t, J=7Hz), 1.2-2.4(12H, m), 2.05(2H, quin, J=6Hz), 4.82(1H, b), 6.20(1H, t, J=5Hz) |
| 3-4 | —C$_2$H$_5$ | ((trans)2-methylcyclohexyl) | 1760, 1460, 1390, 1370, 1340, 1325, 1260 | 0.94(3H, d, J=6Hz), 1.08(3H, t, J=7Hz), 1.0-2.3(9H, m), 2.08(2H, quin, J=6Hz), 4.35(1H, b), 6.23(1H, t, J=5Hz) |
| 3-5 | —C$_2$H$_5$ | —CH$_2$— (cyclohexylmethyl) | 1760, 1450, 1400, 1380, 1360, 1340, 1320, 1250 | 1.05(3H, t, J=7Hz), 1.0-2.4(10H, m), 2.06(2H, quin, J=6Hz), 4.00(2H, d, J=6Hz), 6.21(1H, t, J=5Hz) |
| 3-6 | —(CH$_2$)$_2$CH$_3$ | (cyclopentyl) | 1760, 1470, 1440, 1380, 1350, 1330, 1260 | 0.95(3H, t, J=7Hz), 1.0-2.5(12H, m), 5.15(1H, b), 6.29(1H, t, J=5Hz) |
| 3-7 | —(CH$_2$)$_2$CH$_3$ | (cyclohexyl) | 1760, 1470, 1455, 1380, 1360, 1320, 1260 | 0.95(3H, t, J=7H), 1.0-2.7(14H, m), 4.70(1H, b), 6.27(1H, t, J=5Hz) |
| 3-8 | —(CH$_2$)$_2$CH$_3$ | (cycloheptyl) | 1760, 1460, 1390, 1360, 1260 | 0.95(3H, t, J=7Hz), 1.0-2.5(16H, m), 4.82(1H, b), 6.26(1H, t, J=5Hz) |
| 3-9 | —(CH$_2$)$_2$CH$_3$ | ((trans)-2-methylcyclohexyl) | 1760, 1470, 1450, 1380, 1370, 1355, 1330, 1260 | 0.95(3H, d, J=6Hz), 0.95(3H, t, J=7Hz), 1.0-2.7(13H, m), 4.32(1H, b), 6.27(1H, t, J=5Hz) |

TABLE 3-continued

Formula:

$$Cl-\underset{\underset{R_1}{|}}{CH}-O-\underset{\underset{O}{\|}}{C}-O-R_2$$

| Reference Example No. | $R_1$ | $R_2$ | IR(liquid film) (cm$^{-1}$) | NMR (CDCl$_3$, δ-value) Varian EM-360 (60 MHz) |
|---|---|---|---|---|
| 3-10 | —(CH$_2$)$_2$CH$_3$ | ((endo)-3-norbornyl) | 1765, 1470, 1460, 1380, 1350, 1320, 1310, 1250 | 0.95(3H, t, J=7Hz), 1.0-2.7(14H, m), 4.93(1H, m), 6.27(1H, t, J=5Hz) |
| 3-11 | —CH(CH$_3$)$_2$ | (cyclopentyl) | 1760, 1470, 1440, 1375, 1325, 1260 | 1.06(6H, d, J=7Hz), 1.2-2.7(9H, m), 5.14(1H, b), 6.15(1H, d, J=5Hz) |
| 3-12 | —CH(CH$_3$)$_2$ | (cyclohexyl) | 1760, 1455, 1380, 1360, 1320, 1250 | 1.06(6H, d, J=7Hz), 1.0-2.7(11H, m), 4.70(1H, b), 6.17(1H, d, J=5Hz) |
| 3-13 | —CH(CH$_3$)$_2$ | (cycloheptyl) | 1760, 1460, 1375, 1360, 1320, 1260 | 1.08(6H, d, J=7Hz), 1.2-2.4(3H, m), 4.80(1H, b), 6.13(1H, d, J=5Hz) |
| 3-14 | —CH(CH$_3$)$_2$ | CH$_3$ ((trans)-2-methylcyclohexyl) | 1760, 1450, 1370, 1325, 1260 | 0.94(3H, d, J=6Hz), 1.09 (6H, d, J=7Hz), 1.0-2.3 (10H, m), 4.37(1H, b), 6.17(1H, d, J=5Hz) |

REFERENCE EXAMPLE 4-1

1-Chloro-2-Methylpropyl Chloroformate

A mixture of 18.0 g of isobutyl aldehyde, 1.98 g of pyridine and 50 ml of carbon tetrachloride is cooled to 0° C. and 30 g of phosgene is introduced therein.

Then, the mixture is heated to 34°-40° C. and kept at the same temperature for 1 hour. Excess phosgene is removed by allowing nitrogen gas to pass through the mixture. After the filtration, the solvent is distilled off by distillation under reduced pressure. The residue is subjected to distillation under reduced pressure and the fraction obtained at 57°-59° C./36 mmHg is collected to give 8.9 g of the title compound (yield: 52%).

IR(liquid film) cm$^{-1}$: 1780, 1470, 1395, 1375, 1355, 1140.

NMR(CDCl$_3$, 60 MHz)δ: 1.09(6H, d, J=7 Hz), 1.7-2.7 1H, m), 6.19(1H, d, J=5 Hz).

According to the same procedure as Reference Example 4-1, there can be obtained compounds of Reference Examples 4-2 and 4-3.

REFERENCE EXAMPLE 4-2

1-Chloropropyl Chloroformate

IR(liquid film) cm$^{-1}$: 1780, 1465, 1390, 1140, 1090, 1040.

NMR(CDCl$_3$, 60 MHz)δ: 1.08(3H, t, J=7 Hz), 2.11 (2H, quin, J=6 Hz), 6.28(1H, t, J=5 Hz).

REFERENCE EXAMPLE 4-3

1-Chlorobutyl Chloroformate

IR(liquid film) cm$^{-1}$: 1780, 1690, 1470, 1350, 1140, 1100.

NMR(CDCl$_3$, 60 MHz)δ: 0.97(3H, t, J=7 Hz), 1.1-2.7 (4H, m), 6.28(1H, t, J=5 Hz).

EXAMPLE 1-1

(a) Production of Iodomethyl Cyclohexyl Carbonate

A solution of 0.78 g of chloromethyl cyclohexyl carbonate and 1.0 g of sodium iodide in 15 ml of acetone is stirred at room temperature for 16 hours and then concentrated under reduced pressure. The residue is extracted with ether and the solvent is distilled off under reduced pressure to give the title compound as pale yellow oil.

NMR (CDCl$_3$) δ: 0.7-2.3 (10H, m,

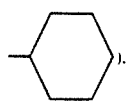

4.70 (1H, m,

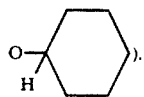

5.95 (2H, s, ICH₂O).

(b) Production of Cyclohexyloxycarbonyloxy 7β-[2-Aminothiazol-4-yl)Acetamido]-3-[[[1-(2-Dimethylaminoethyl)-1H-Tetrazol-5-yl]Thio]Methyl]Ceph-3-Em-4-Carboxylate Dihydrochloride With ice-cooling and stirring, a solution of iodomethyl cyclohexyl carbonate obtained in the above manner (a) in 5 ml of dimethyl formamide is added at one stroke to a solution of 1.8 g of potassium 7β-[2-(2-aminothiazol-4-yl) acetamido]-3-[[[1-(2-dimethylaminoethyl)-1H-tetrazol-5-yl]thio]methyl]ceph-3-em-4-carboxylate in 15 ml of dimethylformamide. The mixture is further stirred for 5 minutes and poured into a mixture of 150 ml of ethyl acetate and 150 ml of ice-cooled 20% aqueous sodium chloride. The organic layer is separated, washed with 150 ml of aqueous sodium chloride and extracted with 40 ml of 1N hydrochloric acid. The extract is subjected to column chromatography on MCI ® Gel CHP20P (75–150 μ, Mitsubishi Chemical Industries, Ltd., Japan), elution being carried out with 0.01N hydrochloride acid or 20% acetonitrile-0.01N hydrochloric acid. The fractions containing the desired product are combined, concentrated under reduced pressure and lyophilized to give 0.70 g of the title compound as a colorless powder.

IR (KBr) cm⁻¹: 1770, 1680, 1630, 15, 1530.
NMR (DMSO-d₆)δ: 1.0–2.0 (10H, m,

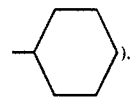

2.84 (6H, s, N(CH₃)2), 3.64 ( CH₂CO), 3.65 (2H, t, J=6 Hz, C-CH₂N), 3.72 & 3.92 (2H, ABq, J=18 Hz, 2-H₂), 4.26 & 4.50 (2H, ABq, J=13 Hz, 3-CH₂), 4.4–4.8 (1H, m,

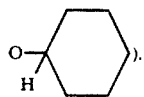

4.79 (2H, t, J=6 Hz, C-CH₂N), 5.15 (1H, d, J=5 Hz, 6-H), 5.71 (1H, d.d, J=5 & 8 Hz, 7-H), 5.76 & 5.90 (2H, ABq, J=6 Hz, OCH₂O), 6.65 (1H, s, thiazole 5-H), 9.24 (1H, d, J=8 Hz, CONH), 9.3 (b), 11.4 (b).

Elemental analysis for C₂₆H₃₅N₉O₇S₃.2HCl.2.5H₂O: Calcd. (%): C, 39.05; H, 5.29; N, 15.76. Found (%): C, 39.02; H, 5.06; N, 16.00.

EXAMPLES 1-2 TO 1-8

The compounds obtained according to the same procedure as Example 1-1 are listed in Table 4 together with their physico-chemical constants.

TABLE 4

Formula

.2HCl

| Example No. | R | (A) Elemental analysis for (B) IR(KBr) (cm⁻¹) | NMR(DMSO-d₆, δ-value) |
|---|---|---|---|
| 1-2 | (cyclopentyl) | (A) C₂₅H₃₃N₉O₇S₃.2HCl.2.5H₂O<br>    C  H  N<br>Calcd: 38.22 5.13 16.04<br>(%)<br>Found: 38.19 5.26 16.31<br>(%)<br>(B)<br>1760, 1680, 1620, 1530, 1370 | 1.8–2.1(8H, m), 2.86(6H, s),<br>3.66(2H, s), 3.67(2H, t, J=6Hz),<br>3.74&3.94(2H, ABq, J=18Hz),<br>4.28&4.52(2H, ABq, J=13Hz ),<br>4.81(2H, t, J=6Hz), 5.06(1H, b)<br>5.16(1H, d, J=5Hz), 5.71(1H, d.d,<br>J=5&8Hz), 5.74&5.90(2H, ABq,<br>J=6Hz), 6.48(1H, s), 9.28(1H, d,<br>J=8Hz), 11.6(b), 9.5(b) |
| 1-3 | (cycloheptyl) | (A) C₂₇H₃₇N₉O₇S₃.2HCl.2.5H₂O<br>    C  H  N<br>Calcd: 39.85 5.45 15.49<br>(%)<br>Found: 37.81 5.66 15.66<br>(%)<br>(B)<br>1780, 1760, 1680, 1620, 1540, 1460, 1420, 1370 | 1.0–2.2(12H, m), 2.85(6H, s),<br>3.66(2H, s), 3.66(2H, t, J=6Hz),<br>3.73&3.95(2H, ABq, J=18Hz),<br>4.28&4.52(2H, ABq, J=13Hz),<br>4.5–5.0(1H, m), 4.81(2H, t,<br>J=6Hz), 5.16(1H, d, J=5Hz), 5.72<br>(1H, d.d, J=5&8Hz), 5.77&5.90<br>(2H, ABq, J=6Hz), 6.68(1H, s),<br>9.28(1H, d, J=8Hz), 9.3(b),<br>11.6(b) |

TABLE 4-continued

Formula

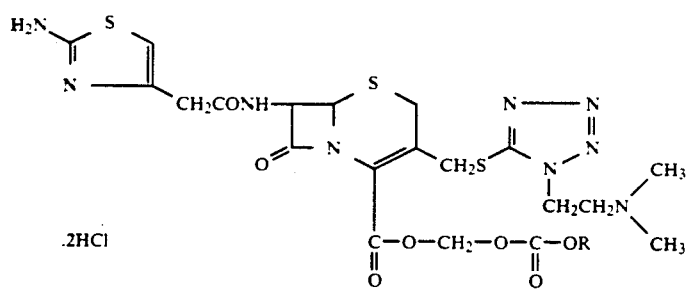

| Example No. | R | (A) Elemental analysis for (B) IR(KBr) (cm$^{-1}$) | NMR(DMSO-d$_6$, δ-value) |
|---|---|---|---|
| 1-4 | 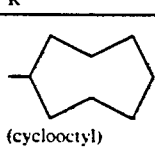<br>(cyclooctyl) | (A)<br>C$_{28}$H$_{39}$N$_9$O$_7$S$_3$·2HCl·2.5H$_2$O<br>    C    H    N<br>Calcd: 40.63 5.60 15.23<br>(%)<br>Found: 40.61 5.65 15.22<br>(%)<br>(B)<br>1760, 1680, 1620, 1530,<br>1450, 1380 | 1.1-2.1(14H, m), 2.84(6H, s),<br>3.64(2H, s), 3.64(2H, t, J=6Hz),<br>3.72&3.93(2H, AB$_q$, J=18Hz), 4.27<br>&4.51(2H, AB$_q$, J=13Hz), 4.80(2H,<br>t, J=6Hz), 4.5–5.0(1H, m), 5.15<br>(1H, d, J=5Hz), 5.71(1H, d.d, J=<br>5&8Hz), 5.76&5.91(2H, AB$_q$, J=<br>6Hz), 9.22(1H, d, J=8Hz), 9.3(b),<br>11.5(b) |
| 1-5 | 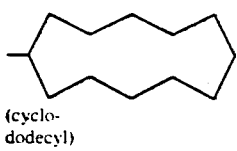<br>(cyclo-<br>dodecyl) | (A)<br>C$_{32}$H$_{47}$N$_9$O$_7$S$_3$·2HCl·3H$_2$O<br>    C    H    N<br>Calcd: 43.04 6.21 14.12<br>(%)<br>Found: 43.06 6.14 14.26<br>(%)<br>(B)<br>1760, 1690, 1625, 1540,<br>1470, 1450, 1380 | 0.8-2.0(22H, m), 2.84(6H, s),<br>3.65(2H, s), 3.66(2H, t, J=6Hz),<br>3.73&3.92(2H, AB$_q$, J=18Hz),<br>4.28&4.51(2H, AB$_q$, J=13Hz),<br>4.80(2H, t, J=6Hz), 5, 71(1H, d.d.<br>J =5&8Hz), 5.16(1H, d, J=5Hz),<br>4.5–5.0(1H, m), 5.76&5.90(2H,<br>AB$_q$, J=6Hz), 6.84(1H, s), 9.25<br>(1H, d, J=8Hz), 9.30(b), 11.5(b) |
| 1-6 | 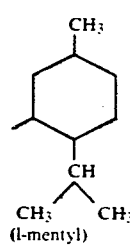<br>(l-mentyl) | (A)<br>C$_{30}$H$_{43}$N$_9$O$_7$S$_3$·2HCl·2.5H$_2$O<br>    C    H    N<br>Calcd: 42.10 5.89 14.78<br>(%)<br>Found: 42.02 6.04 14.71<br>(%)<br>(B)<br>1780, 1760, 1680, 1630,<br>1560, 1460, 1420, 1375 | 0.75(3H, d, J=6Hz), 0.87(6H, d,<br>J=6Hz), 0.6-2.2(8H, m), 2.84<br>6H, s), 3.64(2H, s ), 3.65(2H,<br>t, J=6Hz), 3.73 &3.94(2H, AB$_q$,<br>J=18Hz) 4.0-5.0(1H, m), 4.27&<br>4.51(2H, AB$_q$, J=13Hz), 4.80(2H,<br>t, J=6Hz), 5.16(1H, d, J=5Hz),<br>5.73(1H, d.d, J=5&8Hz), 5.78&5.91<br>(2H, AB$_q$, J=6Hz), 6.64(1H, s),<br>9.24(1H, d, J=8Hz), 9.3(b),<br>11.5(b) |
| 1-7 | 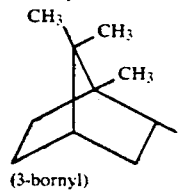<br>(3-bornyl) | (A)<br>C$_{30}$H$_{41}$N$_9$O$_7$S$_3$·2HCl·2.5H$_2$O<br>    C    H    N<br>Calcd: 42.20 5.67 14.61<br>(%)<br>Found: 42.00 5.42 14.83<br>(%)<br>(B)<br>1780, 1680, 1630, 1540,<br>1460, 1420, 1380, 1310 | 0.83, 0.86, 0.88(9H, each s),<br>0.6-2.6(7H, m), 2.84(6H, s),<br>3.65(2H, s), 3.66(2H, t, J=6Hz),<br>3.74&3.95(2H, AB$_q$, J=18Hz),<br>4.29&4.52(2H, AB$_q$, J=13Hz)<br>4.4-5.0(1H, m), 4.80(2H, t, J=<br>6Hz), 5.16(1H, d, J=5Hz), 5.72<br>(1H, d.d, J=5&8Hz), 5.78&5.92<br>(2H, AB$_q$, J=6Hz), 6.66(1H, s),<br>9.26(1H, d, J=8Hz), 9.3(b),<br>11.5(b) |
| 1-8 | 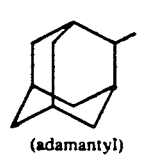<br>(adamantyl) | (A)<br>C$_{30}$H$_{39}$N$_9$O$_7$S$_3$·2HCl·2H$_2$O<br>    C    H    N<br>Calcd: 42.75 5.38 14.96<br>(%)<br>Found: 42.47 5.38 15.00<br>(%)<br>(B)<br>1770, 1680, 1630, 1540,<br>1455, 1420, 1370, 1345 | 1.1-2.6(14H, m), 2.84(6H, s),<br>3.64(2H, s), 3.64(2H, t, J=6Hz),<br>3.71&3.93(2H, AB$_q$, J=18Hz),<br>4.27&4.50(2H, AB$_q$, J=13JHz),<br>4.79(2H, t, J=6Hz), 5.15( 1H,<br>d, J =5Hz), 4.4-5.0(1H, m),<br>5.64(1H, d.d, J=5&8Hz),<br>5.77&5.91(2H, AB$_q$, J=6Hz),<br>6.66(1H, s), 9.24(1H, d, J=8Hz),<br>9.3(b), 11.5(b) |

EXAMPLE 2-1

Method A (a) Production of 1-Iodoethyl Cyclohexyl Carbonate

A solution of 1.65 g of 1-chloroethyl cyclohexyl carbonate and 5.0 g of sodium iodide in 50 ml of acetonitrile is stirred at 70° C. for 45 minutes and then concentrated under reduced pressure. The residue is extracted with ether. The extracts are combined and evaporated under reduced pressure to remove the solvent to give the title compound as pale yellow oil.

NMR (CD$_3$CN, TMS$_{reference}^{external}$) δ: 0.7-2.3 (10H, m,

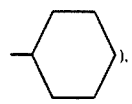), 2.18 (3 J=6 Hz, —CH₃), 4.1–4.9 (1H, m,

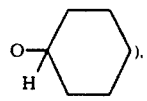), 6.67 (1H, q, J=6 Hz, ICHO).

(b) Production of 1-(Cyclohexyloxycarbonyloxy)Ethyl 7β-[2-(2-Aminothiazol-4-Yl)Acetamido]-3-[[[1-(2-Dimethylaminoethyl-1H-Tetrazol-5-Yl]Thiomethyl]]-Ceph-3-Em-4-Carboxylate Dihydrochloride In 30 ml of dimethylformamide is dissolved 3.6 g of potassium 7β-[2-(2-aminothiazol-4-yl)acetamodo]-3-[[[1-(2-dimethylaminoethyl)-1H-tetrazol-5-yl]thio]methyl]ceph-3-em-4-carboxylate and, with ice-cooling and stirring, a solution of 1-iodoethyl cyclohexyl carbonate obtained in the above manner (a) in 5 ml of dimethylformamide is added at one stroke to the above solution. The mixture is further stirred for 5 minutes and then poured into a mixture of 150 ml of ice-cooled 20% aqueous sodium chloride and 150 ml of ethyl acetate. The organic layer is separated, washed with two 150-ml portions of saturated aqueous sodium chloride and extracted with 40 ml of 1N hydrochloric acid. The extract is subjected to column chromatography on Diaion MCI® CHP 20P (75–150 μ, Mitsubishi Chemical Industries, Ltd., Japan), elution being carried out serially with 0.01N hydrochloric acid and 20% acetonitrile-0.01N hydrochloric acid. The fractions containing the desired product are combined, concentrated under reduced pressure and lyophilized to give 0.96 g of the title compound as a colorless powder.

IR (KBr) cm⁻¹: 1750, 1680, 1620, 1540.
NMR (DMSO-d6) δ: 1.0–2.2 (10H, m,

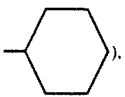), 1.52, 1.55 (3H, d, J=6 Hz,

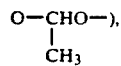), 2.86 (6H, s, N(CH₃)₂), 3.66 (2H, s, CH₂CO), 3.66 (2H, t, J=6 Hz, C—CH₂N), 3.73 & 3.96 (2H, ABq, J=18 Hz, 2—H₂), 4.29 & 4.56, 4.34 (2H, ABq, b.s, J=13 Hz, 3-CH₂), 4.2–4.9 (1H, m,

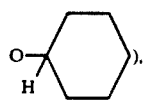), 4.82 (2H, t, J=6 Hz, C—CH₂N), 5.14, 5.18 (1H, each d, J=5 Hz, 6-H), 5.70, 5.75 (1H, each d.d, J=5, 8 Hz, 7-H), 6.68 (1H, s, thiazole 5-H), 6.81, 6.89 (1H, each q, J=6 Hz,

), 9.27, 9.31 (1H, each d, J=8 Hz, CONH), 9.4 (b), 11.6 (b).

Elemental analysis for C₂₇H₃₇N₉O₇S₃.2H₂O; Calcd. (%): C,40.30; H, 5.39; N, 15.66. Found (%): C,40.31; H, 5.32; N, 15.82.

Method B

A solution of 12.5 g of 1-chloroethyl 30 cyclohexyl carbonate and 36 g of sodium iodide in 150 ml of acetonitrile is stirred at 60° C. for 70 minutes and, with ice-cooling, 200 ml of ether and 200 ml of saturated aqueous sodium chloride are added to the solution. The ether layer is taken, washed with 200 ml of saturated aqueous sodium chloride, 50 ml of 5% sodium thiosulfate and 200 ml of saturated aqueous sodium chloride in that order and dried over anhydrous magnesium sulfate. The solvent is then distilled off under reduced pressure to give 1-iodoethyl cyclohexyl carbonate as colorless oil. To this product is added 30 ml of dimethylacetamide to make a solution.

On the other hand, 15 g of potassium 7β-[2-(2-aminothiazol-4-yl)acetamido]-3-[[[1-(2-dimethylaminoethyl)-1H-tetrazol-5-yl]thio]methyl]ceph-3-em-4-carboxylate is dissolved in 150 ml of dimethylacetamide and, with ice-cooling (internal temperature 5° C.), the above-prepared solution of 1-iodoethyl cyclohexyl carbonate in dimethylacetamide is added thereto at one stroke, followed by vigorous stirring for 5 minutes. Then, 100 ml of 2N hydrogen chloride-ether solution is added rapidly and the mixture is stirred for 5 minutes, followed by addition 300 ml of ether to give a glutinous substance. The upper layer is decanted off and 300 ml of ether is added to the glutinous substance, followed by stirring and further removal of the upper layer by decantation (repeated twice). The glutinous substance is dissolved in 200 ml of 1N hydrochloric acid and washed with two 200-ml portions of ethyl acetate. The aqueous layer is subjected to column chromatography on Diaion MCI® GEL CHP20P (70–150 μ, Mitsubishi Chemical Industries, Ltd., Japan), elution being carried out with 5% acetonitrile-0.01N hydrochloric acid and 30% acetonitrile-0.01N hydrochloric acid in that order. The fractions containing the desired product are combined, concentrated under reduced pressure and lyophilized to give 8.0 g of 1-(cyclohexyloxycarbonyloxy)ethyl 7β-[2-(2-aminothiazol-4-yl)acetamido]-3-[[[1-(2-dimethylaminoethyl-1H-tetrazol-5-yl)thio]methyl]ceph-3-em-4-carboxylate dihydrochloride as a colorless powder.

Elemental analysis for C₂₇H₃₇N₉O₇S₃.2HCl.4H₂O, Calcd(%): C, 38.57; H, 5.63; N, 14.99. Found(%): C, 38.35; H, 5.33, N, 14.95.

IR (KBr) cm⁻¹: 1780, 1750, 1680, 1620, 1540.
NMR (Varian EM-390 (90 MHz), DMSO-d6) δ: 1.0–2.2 (10H, m,

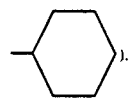

1.52, 1.55 (3H, each d, J=6 Hz,

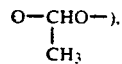

2.85 (6H, s, N(CH₃)₂), 3.66 (2H, s, CH2CO), 3.66 (2H, s, CH2CO), 3.66 (2H, t, J=6 Hz, C—CH₂N), 3.71 & 3.94 (2H, ABq, J=18 Hz, 2-H₂), 4.26 & 4.56, 4.34 (2H, each ABq, b.s, 3-CH₂), 4.2–4.9 (1H, m,

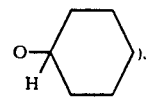

4.82 (2H, t, J=6 Hz, C—CH₂N), 5.13, 5.18 (1H, each d, J=5 Hz, 6-H), 5.70, 5.75 (1H, each d.d, J=5, 8 Hz, 7-H), 6.68 (1H, s, thiazole 5-H), 6.81, 6.89 (1H, each q, J=6 Hz,

9.27, 9.30 (1H, d, J=8 Hz, CONH), 9.0–10.0 (b), 10.5–12.0 (b).

EXAMPLES 2-2 TO 2-20

The compounds obtained according to the same procedure as Method A of Example 2-1 are listed below in Table 5 together with their physico-chemical constants.

TABLE 5

Formula:

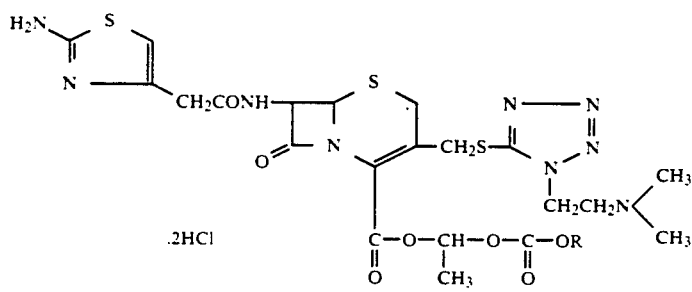

| Example No. | R | (A) Elemental analysis for (B) IR(KBr)(cm⁻¹) | NMR(DMSO-$d_6$, δ-value) |
|---|---|---|---|
| 2-2 | 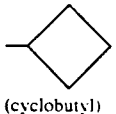 (cyclobutyl) | (A) $C_{25}H_{33}N_9O_7S_3 \cdot 2HCl \cdot 2.5H_2O$<br>C H N<br>Calcd: 38.22 5.13 16.04<br>(%)<br>Found: 38.16 5.09 16.08<br>(%)<br>(B)<br>1780, 1760, 1680, 1625, 1525, 1440, 1380 | 1.51, 1.55(3H, each d, J=6Hz), 1.2–2.6(6H, m), 2.84(6H, s), 3.65(2H, s), 3.66(2H, t, J=6Hz), 3.72&3.93(2H, AB$_q$, J=18Hz), 4.28&4.56, 4.34(2H, each AB$_q$& b.s, J=13Hz), 4.6–5.1(1H, m), 4.80(2H, t, J=6Hz), 5.13, 5.16(1H, each d, J=5Hz), 5.71, 5.75(1H, each d.d, J=5&8Hz), 6.67(1H, s), 6.78, 6.87(1H, each q, J=6Hz), 9.24, 9.28(1H, each d, J=8Hz), 9.3(b), 11.6(b) |
| 2-3 | 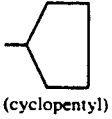 (cyclopentyl) | (A) $C_{26}H_{35}N_9O_7S_3 \cdot 2HCl \cdot 2.5H_2O$<br>C H N<br>Calcd: 39.05 5.29 15.76<br>(%)<br>Found: 38.95 5.32 15.82<br>(%)<br>(B)<br>1780, 1760, 1680, 1630, 1540, 1440, 1380, 1360 | 1.1–2.2(8H, m), 1.51, 1.56(3H, each d, J=5Hz), 2.84(6H, s), 3.64(2H, s), 3.64(2H, t, J=6Hz), 3.72&3.93(2H, AB$_q$, J=8Hz), 4.28&4.54, 4.33(2H, each AB$_q$& b.s, J=13Hz), 4.80(2H, t, J=6Hz), 4.8–5.2(1H, m), 5.13, 5.17(1H, each d, J=5Hz), 5.71, 5.76(1H, each d.d, J=5&8Hz), 6.66(1H, s), 6.80, 6.89(1H, each q, J=5Hz), 9.24, 9.27(1H, each d, J=8Hz), 9.4(b), 11.6(b) |
| 2-4 | 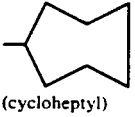 (cycloheptyl) | (A) $C_{28}H_{39}N_9O_7S_3 \cdot 2HCl \cdot 2H_2O$<br>C H N<br>Calcd: 41.07 5.54 15.40<br>(%)<br>Found: 40.95 5.54 15.28<br>(%)<br>(B)<br>1780, 1760, 1680, 1630, 1540, 1450, 1380 | 1.0–2.2(15H, m), 2.84(6H, s), 3.65(2H, s), 3.65(2H, t, J=6Hz), 3.72&3.93(2H, AB$_q$, J=18Hz), 4.26&4.55, 4.33(2H, each AB$_q$& b.s, J=13Hz), 4.80(2H, t, J=6Hz), 4.5–4.9(1H, m), 5.10, 5.17(1H, each d, J=5Hz), 5.71, 5.76(1H, each d.d., J=5&8Hz), 6.66(1H, s), 6.80, 6.89(1H, each q, J=5Hz), 9.24, 9.28(1H, d, J=8Hz), 9.4(b), 11.6(b) |

TABLE 5-continued

Formula

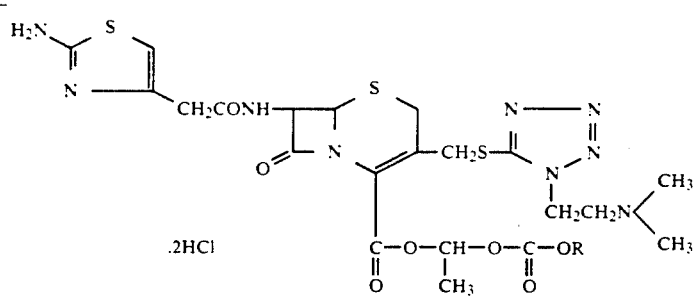

.2HCl

| Example No. | R | (A) Elemental analysis for (B) IR(KBr)(cm$^{-1}$) | NMR(DMSO-d$_6$, δ-value) |
|---|---|---|---|
| 2-5 | 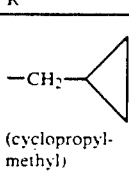<br>—CH$_2$—<br>(cyclopropylmethyl) | (A)<br>C$_{25}$H$_{33}$N$_9$O$_7$S$_3$.2HCl.2.5H$_2$O<br>   C    H    N<br>Calcd: 39.11 4.99 16.42<br>(%)<br>Found: 38.99 5.09 16.27<br>(%)<br>(B)<br>1780, 1760, 1690, 1630,<br>1540, 1450, 1390 | 0.1–0.7(4H, m), 0.8–1.5(1H, m),<br>1.53, 1.57(3H, each d, J=6Hz),<br>2.84(6H, s), 3.66(2H, s),<br>3.66(2H, t, J=6Hz), 3.73&3.93<br>(2H, AB$_q$, J=18Hz), 3.60, 4.00<br>(2H, each d, J=7Hz), 4.28&4.57,<br>4.34(2H, each AB$_q$&b.s, J=13Hz),<br>4.80(2H, t, J=6Hz), 5.14, 5.17<br>(1H, each d, J=5Hz), 5.72,<br>5.76(1H, each d.d, J=5&8Hz),<br>6.66(1H, s), 6.81, 6.90(1H, q,<br>J=6Hz), 9.24, 9.26(1H, each d,<br>J=8Hz), 9.3(b), 11.5(b), |
| 2-6 | 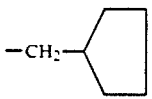<br>—CH$_2$—<br>(cyclopentylmethyl) | (A)<br>C$_{27}$H$_{37}$N$_9$O$_7$S$_3$.2HCl.2H$_2$O<br>   C    H    N<br>Calcd: 40.30 5.39 15.66<br>(%)<br>Found: 40.06 5.08 15.39<br>(%)<br>(B)<br>1780 sh*, 1760, 1680,<br>1625, 1540, 1450, 1395 | 0.9–1.9(8H, m), 1.53, 1.57(3H,<br>each d, J=6Hz), 1.9–2.2(1H, m),<br>2.84(6H, s), 3.64(2H, s), 3.64<br>(2H, t, J=6Hz), 3.72&3.92(2H,<br>AB$_q$, J=18Hz), 3.01, 3.04(2H,<br>each d, J=7Hz), 4.28&4.54,<br>4.34(2H, each AB$_q$&b.s, J=13Hz),<br>4.80(2H, t, J=6Hz), 5.14,<br>5.16(1H, each d, J=5Hz), 5.72,<br>5.76(1H, each d.d, J=5&8Hz),<br>6.65(1H, s), 6.81, 6.90(1H,<br>each q, J=6Hz), 9.22, 9.26(1H,<br>each d, J=8Hz), 9.3(b), 11.5(b) |
| 2-7 | 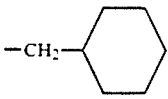<br>—CH$_2$—<br>(cyclohexylmethyl) | (A)<br>C$_{28}$H$_{39}$N$_9$O$_7$S$_3$.2HCl.2H$_2$O<br>   C    H    N<br>Calcd: 41.07 5.54 15.40<br>(%)<br>Found: 41.03 5.38 15.40<br>(%)<br>(B)<br>1780, 1760, 1680, 1625,<br>1540, 1450, 1390, 1360 | 0.6–2.0(11H, m), 1.52, 1.56(3H,<br>each d, J=5Hz), 2.84(6H, s),<br>3.64(2H, s), 3.66(2H, t, J=6Hz),<br>3.73&3.94(2H, AB$_q$, J=18Hz),<br>3.94, 3.97(2H, each d, J=6Hz),<br>4.27&4.55, 4.34(2H, each AB$_q$&<br>b.s, J=13Hz), 4.80(2H, t, J=6Hz),<br>5.14, 5.16(1H, each d, J=5Hz),<br>5.71, 5.75(1H, each d.d, J=5&<br>8Hz), 6.66(1H, s), 6.80,<br>6.90(1H, each q, J–5Hz), 9.25,<br>9.29(1H, each d, J=8Hz), 11.6(b),<br>9.4(b) |
| 2-8 | 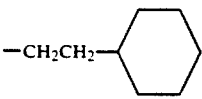<br>—CH$_2$CH$_2$—<br>(2-cyclohexylethyl) | (A)<br>C$_{29}$H$_{41}$N$_9$O$_7$S$_3$.2HCl.2.5H$_2$O<br>   C    H    N<br>Calcd: 41.48 5.52 15.01<br>(%)<br>Found: 41.51 5.76 15.24<br>(%)<br>(B)<br>1780, 1760, 1680, 1630,<br>1540, 1450, 1400, 1360 | 0.6–1.9(12H, m), 1.52, 1.56(3H,<br>each d, J=5Hz), 2.84(6H, s),<br>3.65(2H, s), 3.66(2H, b, J=6Hz),<br>3.72&3.93(2H, AB$_q$, J=18Hz),<br>4.0–4.3(2H, m), 4.28&4.56,<br>4.33(2H, each AB$_q$&b.s, J=13Hz),<br>5.80(2H, t, J=6Hz), 5.14,<br>5.17(1H, J=5Hz, each d), 5.70,<br>5.77(1H, each d.d, J=5&8Hz),<br>6.66(1H, s), 6.80, 6.90(1H,<br>each q, J=5Hz), 5.24, 5.27(1H,<br>each d, J=8Hz), 9.3(b),<br>11.5(b) |
| 2-9 | 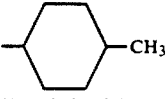<br>—⟨⟩—CH$_3$<br>(4-methylcyclohexyl) | (A)<br>C$_{28}$H$_{39}$N$_9$O$_7$S$_3$.2HCl.3H$_2$O<br>   C    H    N<br>Calcd: 40.19 5.66 15.06<br>(%)<br>Found: 40.30 5.66 15.11<br>(%)<br>(B)<br>1780, 1760, 1680, 1630,<br>1540, 1450, 1380 | 0.88(3H, t), 0.6–2.2(9H, m),<br>1.51, 1.54(3H, each d, J=6Hz),<br>2.84(6H, s), 3.64(2H, s),<br>3.65(2H, t, J=6H), 3.72&3.91(2H,<br>AB$_q$, J=18Hz), 4.0–5.0(1H, m),<br>4.26&4.53, 4.33(2H, each AB$_q$&<br>b.s, J=13Hz), 4.80(2H, t, J=6Hz),<br>5.13, 5.16(1H, each d, J=5Hz),<br>5.71, 5.75(1H, each d.d, J=5&<br>8Hz), 6.66(1H, s), 6.80,<br>6.88(1H, each q, J=6Hz), 9.22, |

TABLE 5-continued

Formula:

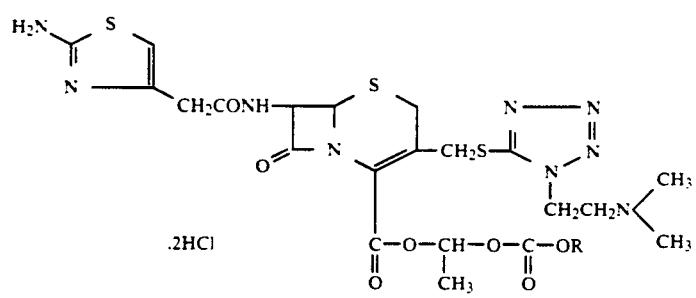

| Example No. | R | (A) Elemental analysis for (B) IR(KBr)(cm$^{-1}$) | NMR(DMSO-d$_6$, δ-value) |
|---|---|---|---|
| | | | 9.26(1H, each d, J=8Hz), 9.3(b), 11.5(b) |
| 2-10 | (3-methylcyclohexyl) | (A) C$_{28}$H$_{39}$N$_9$O$_7$S$_3$.2HCl.3H$_2$O     C   H   N Calcd: 40.19 5.66 15.06 (%) Found: 40.41 5.69 15.25 (%) (B) 1780, 1760, 1680, 1630, 1540, 1450, 1380 | 0.91(3H, d, J=6Hz), 1.51, 1.56(1H, d, J=6Hz), 0.6-2.2(9H, m), 2.84(6H, s), 3.65(2H, s), 3.66(2H, t, J=6Hz), 3.73&3.93 (2H, AB$_q$, J=18 Hz), 4.0-5.0(1H, m), 4.27&4.55, 4.33(2H, each AB$_q$&b.s, J=13Hz), 4.80(2H, t, J=6Hz), 5.13, 5.17(1H, each d, J=5Hz), 5.71, 5.76(1H, each d.d, J=5&8Hz), 6.66(1H, s), 6.81, 6.89(1H, each q, J=6Hz), 9.23, 9.26(1H, each d, J=8Hz), 9.3(b), 11.5(b) |
| 2-11 | (2-methylcyclohexyl) | (A) C$_{28}$H$_{39}$N$_9$O$_7$S$_3$.2HCl.3H$_2$O     C   H   N Calcd: 40.19 5.66 15.06 (%) Found: 40.25 5.56 15.03 (%) (B) 1780, 1760, 1680, 1630, 1540, 1450, 1380 | 0.86, 0.89(3H, each d, J=6Hz), 0.7-2.2(9H, m), 1.52, 1.56(3H, each d, J=6Hz), 2.84(6H, s), 3.65(2H, s), 3.65(2H, t, J=6Hz), 3.72&3.93(2H, AB$_q$, J=18Hz), 4.27&4.55, 4.33(2H, each AB$_q$& b.s, J=13Hz), 4.80(2H, t, J=6Hz), 4.0-5.0(1H, m), 5.13, 5.16(1H, each d.d, J=5Hz), 5.69, 5.75(1H, each d.d, J=5&8Hz), 6.66(1H, s), 6.81, 6.91(1H, each q, J=6Hz), 9.23, 9.26(1H, each d, J=8Hz), 9.3(b), 11.5(b) |
| 2-12 | ((cis)-2-methylcyclohexyl) | (A) C$_{28}$H$_{39}$N$_9$O$_7$S$_3$.2HCl.3H$_2$O     C   H   N Calcd: 40.63 5.60 15.23 (%) Found: 40.81 5.52 15.49 (%) (B) 1785, 1760, 1680, 1630, 1540, 1450, 1385 | 0.83(3H, d, J=6Hz), 0.8-2.2(9H, m), 1.53, 1.57(3H, each d, J= 6Hz), 2.84(6H, s), 3.65(2H, s), 3.66(2H, t, J=6Hz), 3.72&3.92 (2H, AB$_q$, J=18Hz), 4.26&4.54, 4.33(2H, each AB$_q$&b.s, J=13Hz), 4.5-5.0(1H, m), 4.80(2H, t, J= 6Hz), 5.13, 5.15(1H, each d, J= 5Hz), 5.69, 5.73(1H, each d.d, J=5&8Hz), 6.66(1H, s), 6.80, 6.89(1H, each q, J=6Hz), 9.24 (1H, each d, J=8Hz), 9.3(b), 11.6(b) |
| 2-13 | ((trans)-2-methylcyclohexyl) | (A) C$_{28}$H$_{39}$N$_9$O$_7$S$_3$.2HCl.2.5H$_2$O     C   H   N Calcd: 40.63 5.60 15.23 (%) Found: 40.71 5.52 15.45 (%) (B) 1780, 1760, 1690, 1625, 1540, 1450, 1380, 1360 | 0.89(3H, d, J=6Hz), 1.51, 1.55 (3H, each d, J=6Hz), 0.8~2.2 (9H, m), 2.84(6H, s), 3.64(2H, s), 3.64(2H, t, J=6Hz), 3.71&3.91 (2H, AB$_q$, J=18Hz), 4.26&4.54, 4.82(2H, each AB$_q$&b.s, J=13Hz), 4.0-4.6(1H, m), 4.89(2H, t, J= 6Hz), 5.13, 5.16(1H, each d, J=5Hz), 5.70, 5.75(1H, each d.d, J=5&8Hz), 6.66(1H, s), 5.80, 6.90(1H, q, J=6Hz), 9.22, 9.25(1H, each d, J=5Hz), 9.3(b), 11.5(b) |

TABLE 5-continued

Formula

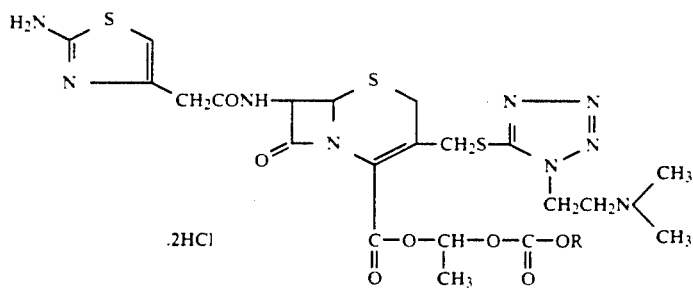
.2HCl

| Example No | R | (A) Elemental analysis for (B) IR(KBr)(cm$^{-1}$) | NMR(DMSO-d$_6$, δ-value) |
|---|---|---|---|
| 2-14 | 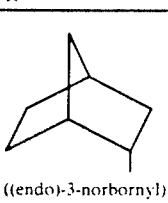<br>((endo)-3-norbornyl) | (A)<br>C$_{28}$H$_{37}$N$_9$O$_7$S$_3$.2HCl.2H$_2$O<br>   C  H  N<br>Calcd: 41.17 5.31 15.43<br>(%)<br>Found: 41.30 5.31 15.28<br>(%)<br>(B)<br>1780, 1760, 1690, 1625, 1535, 1450, 1380, 1310 | 0.8-2.5(10H, m), 1.51, 1.55(3H, d, J=6Hz), 2.83(6H, s), 3.63(2H, s), 3.63(2H, t, J=6Hz), 3.71& 3.91(2H, AB$_q$, J=18Hz), 4.25& 4.54, 4.32(2H, each AB$_q$&b.s, J= 13Hz), 4.78(2H, t, J=6Hz), 4.5- 5.1(1H, m), 5.12, 5.15(1H, each d, J=5Hz), 5.71, 5.75(1H, each d.d, J=5&8Hz), 6.65(1H, s), 6.79, 6.90(1H, each q, J=6Hz), 9.20, 9.24(1H, each d, J=8Hz), 9.3(b), 11.5(b) |
| 2-15 | 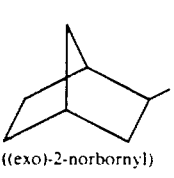<br>((exo)-2-norbornyl) | (A)<br>C$_{28}$H$_{37}$N$_9$O$_7$S$_3$.2HCl.2.5H$_2$O<br>   C  H  N<br>Calcd: 40.78 5.37 15.27<br>(%)<br>Found: 40.87 5.13 15.13<br>(%)<br>(B)<br>1785, 1760, 1690, 1630, 1530, 1455, 1380, 1315 | 0.8-2.5(10H, m), 1.51, 1.55(3H, each d, J=6Hz), 2.84(6H, s), 3.64(2H, s), 3.64(2H, t, J=6Hz), 3.78&3.92(2H, AB$_q$, J=18Hz), 4.26&4.54(2H, AB$_q$, J=13Hz), 4.2-4.8(1H, m), 4.80(2H, t, J= 6Hz), 5.03, 5.06(1H, each d, J=5Hz), 5.73, 5.76(1H, each d.d, J=5&8Hz), 6.64(1H, s), 6.80, 6.89(1H, each q, J=6Hz), 9.20, 9.24(1H, each d, J=8Hz), 9.3(b), 11.5(b) |
| 2-16 | 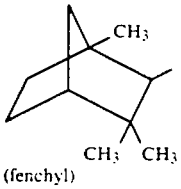<br>(fenchyl) | (A)<br>C$_{31}$H$_{43}$N$_9$O$_7$S$_3$.2HCl.2.5H$_2$O<br>   C  H  N<br>Calcd: 42.90 5.81 14.53<br>(%)<br>Found: 42.71 5.62 14.59<br>(%)<br>(B)<br>1780, 1760, 1690, 1630, 1540, 1450, 1380 | 0.80(3H, s), 1.08(6H, s), 0.8-2.0 (7H, m), 1.55, 1.59(3H, each d, J=6Hz), 2.84(6H, s), 3.64(2H, s), 3.66(2H, t, J=6Hz), 3.73&3.92 (2H, AB$_q$, J=18Hz), 4.22(1H, b.s), 4.28&4.57(2H, AB$_q$, J=13Hz), 4.80(2H, t, J=6Hz), 5.14, 5.16 (1H, each d, J=5Hz), 5.68, 5.75(1H, each d.d, J=5&8Hz), 6.66(1H, s), 6.83, 6.88(1H, each q, J=6Hz), 9.24, 9.28(1H, each d, J=8Hz), 9.3(b), 11.5(b) |
| 2-17 | 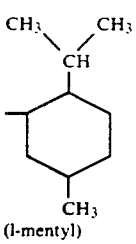<br>(l-mentyl) | (A)<br>C$_{31}$H$_{45}$N$_9$O$_7$S$_3$.2HCl.2.5H$_2$O<br>   C  H  N<br>Calcd: 42.80 6.02 14.49<br>(%)<br>Found: 48.02 5.84 14.47<br>(%)<br>(B)<br>1785, 1760, 1690, 1630, 1540, 1450, 1380 | 0.70, 0.78(3H, each d, J=6Hz), 0.89(6H, d, J=6Hz), 1.52, 1.57 (3H, each d, J=6Hz), 0.6-2.2 (9H, m), 2.85(6H, s), 3.66(2H, s), 3.66(2H, t, J=6Hz), 3.78&3.98 (2H, AB$_q$, J=18Hz), 4.25&4.55, 4.83(2H, AB$_q$&b.s, J=13Hz), 4.0-5.0(1H, m), 4.80(2H, t, J= 6Hz), 5.13, 5.16(1H, each d, J=5Hz), 5.71, 5.74(1H, each d.d, J=5&8Hz), 6.65, 6.66(1H, each s), 6.80, 6.86(1H, each q, J= 6Hz), 9.22, 9.28(1H, each d, J=8Hz), 9.3(b), 11.4(b) |
| 2-18 | 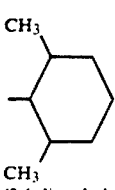<br>(2,6-dimethyl-cyclohexyl) | (A)<br>C$_{29}$H$_{41}$N$_9$O$_7$S$_3$.2HCl.2H$_2$O<br>   C  H  N<br>Calcd: 41.82 5.69 15.14<br>(%)<br>Found: 41.68 5.65 14.90<br>(%)<br>(B)<br>1785, 1760, 1690, 1630, 1540, 1450, 1385 | 0.84(6H, d, J=7Hz), 0.6-2.2(8H, m), 1.54, 1.58(3H, each d, J=6Hz), 2.84(6H, s), 3.64(2H, s), 3.65(2H, t, J=6Hz), 3.72& 3.91(2H, AB$_q$, J=18Hz), 4.1-4.9 (1H, m), 4.24&4.54, 4.36(2H, AB$_q$&b.s, J=13Hz), 4.79(2H, t, J= 6Hz), 5.14(1H, d, J=5Hz), 5.70, 5.76(1H, each d.d, J=5&8Hz), 6.66(1H, s), 6.80, 6.88(1H, q, J=6Hz), 9.21, 9.24(1H, each d, J=8Hz), 9.2(b), 11.4(b) |

TABLE 5-continued

Formula:

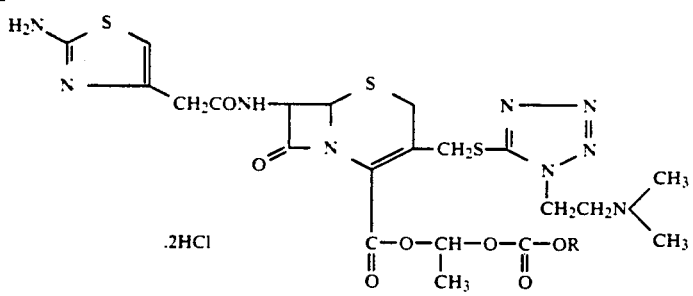

| Example No | R | (A) Elemental analysis for (B) IR(KBr)(cm⁻¹) | NMR(DMSO-d₆, δ-value) |
|---|---|---|---|
| 2-19 | CH₃<br>\|<br>CH<br>/<br>(cyclohexyl)<br>(1-cyclohexylethyl) | (A)<br>C₂₉H₄₁N₉O₇S₃.2HCl.2H₂O<br>    C   H   N<br>Calcd: 41.82 5.69 15.14<br>(%)<br>Found: 41.61 5.85 14.94<br>(%)<br>(B)<br>1785, 1760, 1690, 1630, 1540, 1455, 1380 | 1.20(3H, d, J=6Hz), 1.52, 1.55 (3H, each d, J=6Hz), 2.84(6H, s), 3.64(2H, s), 3.64(2H, t, J=6Hz), 3.72&3.92(2H, ABq, J=18Hz), 4.26&4.54, 4.38(2H, each AB<sub>q</sub>& b.s, J=13Hz), 4.0–4.9(1H, m), 4.79(2H, t, J=6Hz), 5.14, 5.16 (1H, each d, J=5Hz), 5.71, 5.75 (1H, each d.d, J=5&8Hz), 6.65 (1H, s), 6.81, 6.89(1H, each q, J=6Hz), 9.21, 9.25(1H, each d, J=8Hz), 9.3(b.s), 11.5(b.s) |
| 2-20 | CH₂CH₃<br>\|<br>(cyclohexyl)<br>(2-ethylcyclohexyl) | (A)<br>C₂₉H₄₁N₉O₇S₃.2HCl.2.5H₂O<br>    C   H   N<br>Calcd: 41.38 5.75 14.97<br>(%)<br>Found: 41.14 5.57 15.14<br>(%)<br>(B)<br>1780, 1760, 1680, 1625, 1535, 1450, 1380 | 0.85(3H, t, J=6H), 1.52, 1.56 (3H, each d, J=6Hz), 0.6–2.2 (11H, m), 2.85(6H, s), 3.65(2H, s), 3.65(2H, t, J=6Hz), 3.72& 3.92(2H, ABq, J=18Hz), 4.28& 4.56, 4.33(2H, each ABq&b.s), 4.79(2H, t, J=6Hz), 4–5(1H, b.s), 5.12, 5.15(1H, each d, J=5Hz), 5.68, 5.74(1H, each d.d, J=5& 8Hz), 6.65(1H, s), 6.79, 6.89 (1H, q, J=6Hz), 9.22, 9.26(1H, each d, J=8Hz), 9.2(b), 11.5(b) |

*sh means shoulder

EXAMPLE 3-1

1-(Cyclohexyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride.dihydrate (0.5 g) as obtained in Example 2-1 is subjected to column chromatography on Diaion MCI® Gel CHP 20P (75–150 μ, Mitsubishi Chemical Industries, Ltd., Japan), elution being carried out with 20% acetonitrile-0.01N hydrochloric acid. The eluate fractions (780–900 ml) are combined and lyophilized to give 190 mg of a colorless powder. This product is one of the diastereomers with respect to the asymmetric carbon atom in the ester moiety of the compound as obtained in Example 2-1.

$[\alpha]_D^{22}+36.7°$ (c=0.215, H₂O).

IR (KBr) cm⁻¹: 1790, 1760, 1695, 1680, 1630, 1540.

NMR (DMSO-d6) δ: 0.9–2.1 (10H, m,

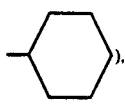

1.55 (3H, d, J=6 Hz, CH₃), 2.83.(6H, s, N(CH₃)₂), 3.62 (2H, s, CH₂CON), 3.64 (2H, t, J=6 Hz, C—CH₂N), 3.69 & 3.91 (2H, ABq, J=18 Hz, 2-H₂), 4.27 & 4.53 (2H, ABq, J=13 Hz, 3-CH₂), 4.0–5.0 (1H, m,

4.78 (2H, t, J=6 Hz, C—CH₂N), 5.12 (1H, d, J=5 Hz, 6-H), 5.71 (1H, d.d, J=5 & 8 Hz, 7-H), 6.65 (1H, s, thiazole 5-H), 6.90 (1H,q, J=6 Hz,

9.29 (1H, d, J=8 Hz, CONH), 9.3 (b), 11.5 (b).

Elemental analysis for C₂₇H₃₇N₉O₇S₃.2HCl.3H₂O: Calcd. (%): C, 39.41; H, 5.51; N, 15.32. Found (%): C, 39.49, H, 5.60; N, 15.23.

EXAMPLE 3-2

The 1000–1160 ml eluate fractions obtained by the above column chromatography in Example 3-1 are lyophilized to give 70 mg of colorless powder. This product is the diastereomer counterpart of the product of Example 3-1.

$[\alpha]_D^{22}+62.9$ (c=0.24, H₂O).

IR (KBr) cm⁻¹: 1780, 1760, 1680, 1625, 1540.

NMR (DMSO-d6) δ: 0.9–2.1 (10H, m,

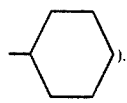

1.51 (3H, d. J=6 Hz, CH₃), 2.82 (6H, s, N(CH₃)₂), 3.63 (2H, s, CH₂CO), 3.64 (2H, t, J=6 Hz, C—CH₂N), 3.72 & 3.92 (2H, ABq, J=18 Hz, 2-H₂), 4.30 (2H, b.s, 3-CH₂), 4.2–5.0 (1H, m,

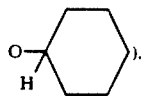

4.78 (2H, t, J=6 Hz, C—CH₂N), 5.16 (1H, d, J=5 Hz, 6-H), 5.76 (1H, d.d, J=5 & 8 Hz, 7-H), 6.66 (1H, s, thiazole 5-H), 6.80 (1H, q, J=6 Hz,

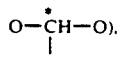

9.22 (1H, d, J=8 Hz, CONH), 9.3 (b), 11.5 (b).

Elemental analysis for C₂₇H₃₇N₉O₇S₃·2HCl·3H₂O: Calcd. (%): C, 39.41; H, 5.51; N, 15.32. Found (%): C, 39.42; H, 5.60; N, 15.09.

EXAMPLE 4-1

(a) Production of 1-Iodoethyl 3,3,5-Trimethylcyclohexyl Carbonate

Acetonitrile (250 ml) is warmed to 50° C. and 38 g of sodium iodide is added and dissolved, followed by addition of 14 g of 1-chloroethyl 3,3,5-trimethylcyclohexyl carbonate. The mixture is stirred for 2 hours, poured into 250 ml of ice-water and extracted with two 200-ml portions of ethyl acetate. The extracts are combined, washed with 150 ml of 5% aqueous sodium thiosulfate, 300 ml of water and 300 ml of saturated aqueous sodium chloride (twice) in that order and dried over anhydrous sodium sulfate. The solvent is then distilled off under reduced pressure to to give the title compound as oil.

NMR (CDCl₃) δ: 2.25 (3H, d, J=6 Hz,

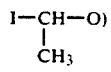

(b) Production of 1-(3,3,5-Trimethylcyclohexyloxycarbonyloxy)Ethyl 7β-[2-(2-Aminothiazol-4-Yl)Acetamido]-3-[[[1-(2-Dimethylaminoethyl)-1H-Tetrazol-5-Yl]Thio]Methyl]-Ceph-3-Em-4-Carboxylate In 80 ml of dimethylacetamide is dissolved 5.6 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate and the solution is cooled to −5° C.

With stirring, 1-iodoethyl 3,3,5-trimethylcyclohexyl carbonate as obtained in the above manner (a) is added to the solution at one stroke. The mixture is stirred for 5 minutes and poured into a mixture of 300 ml of ethyl acetate and 200 ml of ice-water. The organic layer is taken and the aqueous layer is further extracted with 200 ml of ethyl acetate. These organic layers are combined, washed with three 150-ml portions of ice-water and three 150-ml portions of saturated aqueous sodium chloride in that order and dried over anhydrous magnesium sulfate. The solvent is then distilled off under reduced pressure and isopropyl ether is added to the residue. The thus-obtained white powder is collected by filtration, washed with isopropyl ether and dried to give the title compound.

IR (KBr) cm⁻¹: 1780, 1760, 1680, 1620, 1525, 1460, 1380.

NMR (Varian EM 390 (90 MHz), CDCl₃) δ: 0.55–2.3 (16H, m), 1.56, 1.60 (3H, each d, J=6 Hz), 2.26 (6H, s), 2.76 (2H, t, J=6H), 3.5 (2H, s), 3.70 (2H, m), 4.13–4.53 (3H, m), 4.94, 4.96 (1H, each d, J=4.5 Hz), 5.33 (2H, b.s), 5.86 (1H, m), 6.26 (1H, s), 6.95 (1H, m), 7.98, 8.05 (1H, each d, J=9 Hz).

Elemental analysis for C₃₀H₄₃N₉O₇S₃: Calcd.(%): C, 48.83; H, 5.87; N, 17.08. Found (%): C, 48.71; H, 5.85; N, 17.05.

EXAMPLE 5-1

(a) Production of 1-Iodopropyl Cyclopentyl Carbonate

A solution of 3.11 g of 1-chloropropyl cyclopentyl carbonate and 6 g of sodium iodide in 40 ml of acetonitrile is stirred at 60° C. for 60 minutes and then concentrated under reduced pressure. The residue obtained is distributed with 100 ml of ether and 100 ml of water. The ether layer is separated, washed serially with 50 ml of 5% sodium thiosulfate and 100 ml of saturated aqueous solution of sodium chloride, and dried over anhydrous magnesium sulfate. The solvent is distilled off under reduced pressure to give the title compound as oily material.

(b) Production of 1-(Cyclopentyloxycarbonyloxy)Propyl 7β-[2-(2-Aminothiazol-4-Yl)Acetamido]-3-[[[1-(2-Dimethylaminoethyl)-1H-Tetrazol-5-Yl]Thio]Methyl]-Ceph-3-Em-4-Carboxylate Dihydrochloride With ice-cooling and stirring, a solution of 1-iodopropyl cyclopentyl carbonate obtained in the same manner (a) in 10 ml of dimethylformamide is added at one stroke to a solution of 1.2 g of potassium 7β-[2-(2-aminothiazol-4-yl)acetamido]-3-[[[1-(2-dimethylaminoethyl)-1H-tetrazol-5-yl]thio]methyl]ceph-3-em-4-carboxylate in 8 ml of dimethylformamide. The mixture is stirred violently for 5 minutes. Then, 20 ml of 2N hydrogen chloride-ether solution is added to the mixture. After stirring for 5 minutes, 150 ml of ether is added to the mixture and the upper layer is removed by decantation (this procedure is conducted twice).

After dissolving the glutinous material obtained in 20 ml of 0.1N hydrochloric acid, the solution is subjected to column chromatography on Diaion MCI ® Gel CHP 20P (150–300 μ, Mitsubishi Chemical Industries, Ltd., Japan), elution being carried out serially with 10% acrylonitrile/0.01N hydrochloric acid and 40% acrylonitrile/0.01N hydrochloric acid. The fractions containing the desired product are combined, concentrated under reduced pressure and lyophilized to give 0.2 g of the title compound as a colorless powder.

IR(KBr) cm⁻¹: 1780, 1760, 1680, 1620, 1530, 1380, 1320.

NMR (DMSO-d6) δ: 0.94 (3H., t, J=7 Hz), 1.1–2.1 (10H, m), 2.84 (6H, s), 3.65 (2H, s), 3.65(2H, t, J=6 Hz), 3.73 & 3.92 (2H, ABq, J=18 Hz), 4.26 & 4.52, 4.33 (2H, each ABq & b. s, J=13 Hz), 4.80 (2H, t, J=6 Hz), 5.02

(1H, b), 5.14, 5.17 (1H, each d, J=5 Hz), 5.71, 5.76 (1H, each d.d, J=5 & 8 Hz), 6.66 (1H, s), 6.69, 6.76, (1H, each t, J=5 Hz), 9.24, 9.28 (1H, each d, J=8 Hz).

Elemental analysis for $C_{27}H_{37}N_9O_7S_3.2HCl.2.5H_2O$: Calcd. (%): C, 39.85; H, 5.45; N, 15.49. Found (%): C, 39.68, H, 5.35; N, 15.55.

EXAMPLES 5-2 – 5-14

The compounds obtained according to the same procedure as Example 5-1 are listed below in Table 6 together with their physico-chemical constants.

TABLE 6

Formula:

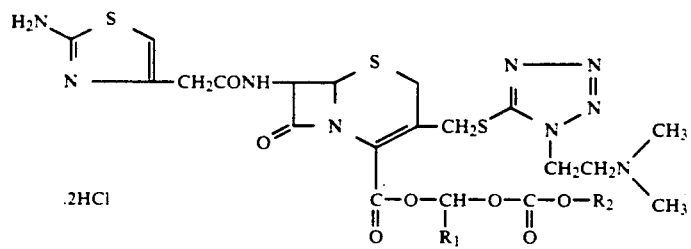

.2HCl

| Example No. | $R_1$ | $R_2$ | (A) Elemental analysis for<br>(B) IR (KBr) (cm$^{-1}$) | NMR (DMSO-$d_6$, δ-value) |
|---|---|---|---|---|
| 5-2 | —$C_2H_5$ | (cyclohexyl) | (A) $C_{28}H_{39}N_9O_7S_3.2HCl.3H_2O$<br>　　C　H　N<br>Calcd: 40.19 5.66 15.06 (%)<br>Found: 40.11 5.24 15.11 (%)<br>(B) 1780, 1755, 1680<br>　　1625, 1530, 1445<br>　　1380 | 0.94(3H, t, J=7Hz), 1.0–2.1(12H, m), 2.85 (6H, s), 3.64(2H, s), 3.63(2H, t, J=6Hz), 3.72&3.92(2H, AB$_q$, J=18Hz), 4.25&4.51, 4.31 (2H, each AB$_q$& b.s, J=13Hz), 4.57 (1H, b), 4.78(2H, t, J=6Hz), 5.12, 5.16 (1H, each d, J=5Hz), 5.71, 5.75(1H, each d.d, J=5&8Hz), 6.65 (1H, s), 6.69, 6.76 (1H, each t, J=5Hz), 9.21, 9.25(1H, each d, J=8Hz) |
| 5-3 | —$C_2H_5$ | (cycloheptyl) | (A) $C_{29}H_{41}N_9O_7S_3.2HCl.2H_2O$<br>　　C　H　N<br>Calcd: 41.82 5.69 15.14 (%)<br>Found: 41.66 5.38 15.26 (%)<br>(B) 1780, 1755, 1680<br>　　1625, 1540, 1460<br>　　1390 | 0.95(3H, t, J=7Hz), 1.5–2.2(14H, m), 2.85(6H, s), 3.65 (2H, s), 3.64(2H, t, J=6Hz), 3.73& 3.93(2H, AB$_q$, J=18 Hz), 4.27&4.53, 4.33(2H, each AB$_q$ &b.s, J=13Hz), 4.80(2H, t, J=6Hz), 4.6–5.0(1H, b), 5.14, 5.17(1H, each d, J=5Hz), 5.72, 5.77(1H, each d.d, J=5&8Hz), 6.66(1H, s), 6.69, 6.77(1H, each t, J=5Hz), 9.24, 9.27 (1H, each d, J=8Hz) |
| 5-4 | —$C_2H_5$ | $CH_3$<br>((trans)-2-methylcyclohexyl) | (A) $C_{29}H_{41}N_9O_7S_3.2HCl.2.5H_2O$<br>　　C　H　N<br>Calcd: 41.38 5.75 14.97 (%)<br>Found: 41.52 5.57 14.97 (%)<br>(B) 1780, 1755, 1680<br>　　1625, 1540, 1455<br>　　1390 | 0.89(3H, d, J=6Hz), 0.94(3H, t, J=7Hz), 1.0–2.1(11H, m), 2.84(6H, s), 3.64 (2H, s), 3.64(2H, t, J=6Hz), 3.72&3.90 (2H, AB$_q$, J=18Hz), 4.28&4.52, 4.32(2H, each AB$_q$&b.s, J=13 Hz), 4.2–4.9(1H, b), 4.79(2H, t, J=6Hz), 5.14, 5.16(1H, each d, J=5Hz), 5.72, 5.76 (1H, each d.d, J=5&8 Hz), 6.66(1H, s), 6.69, 6.78(1H, each t, J=5Hz), 9.22, 9.26 (1H, each d, J=8Hz) |

TABLE 6-continued

Formula

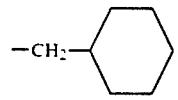

| Example No. | R₁ | R₂ | (A) Elemental analysis for (B) IR (KBr) (cm⁻¹) | NMR (DMSO-d₆, δ-value) |
|---|---|---|---|---|
| 5-5 | —C₂H₅ | —CH₂— 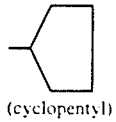 (cyclohexylmethyl) | (A) C₂₉H₄₁N₉O₇S₃.2HCl.2.5H₂O  C   H   N Calcd: 41.38 5.75 14.97 (%) Found: 41.46 5.76 15.30 (%) (B) 1780, 1760, 1680 1620, 1540, 1450 1390 | 0.95(3H, t, J=7Hz), 0.9-2.1(13H, m), 2.85(6H, s), 3.64 (2H, s), 3.65(2H, t, J=6Hz), 3.74&3.94 (2H, AB_q, J=18Hz), 3.94, 3.97(2H, each d, J=6Hz), 4.26& 4.52, 4.33(2H, each AB_q&b.s, J=13Hz), 4.80(2H, t, J=6Hz), 5.14, 5.16(1H, each d, J=5Hz), 5.73, 5.77(1H, each d.d, J=5&8Hz), 6.66(1H, s), 6.69, 6.77(1H, each t, J=5Hz), 9.24, 9.27(1H, each d, J=8Hz) |
| 5-6 | —(CH₂)₂CH₃ | 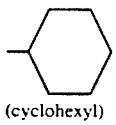 (cyclopentyl) | (A) C₂₈H₃₉N₉O₇S₃.2HCl.1.5H₂O  C   H   N Calcd: 41.53 5.48 15.57 (%) Found: 41.44 5.55 15.62 (%) (B) 1780, 1760, 1680 1625, 1540, 1430 1380 | 0.91, 0.93(3H, each t, J=6Hz), 1.0-2.1 (12H, m), 2.84(6H, s), 3.64(2H, s), 3.66(2H, t, J=6Hz), 3.72&3.90(2H, AB_q, J=18Hz), 4.27&4.52, 4.32(2H, each AB_q& b.s, J=13Hz), 4.80 (2H, t, J=6Hz), 5.02(1H, b), 5.13, 5.16(1H, each d, J= 5Hz), 5.71, 5.76 1H, each d.d, J=5&8 Hz), 6.65(1H, s), 6.73, 6.81(1H, each t, J=5Hz), 9.22, 9.25(1H, each d, J= 8Hz) |
| 5-7 | —(CH₂)₂CH₃ | 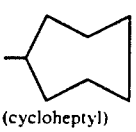 (cyclohexyl) | (A) C₂₉H₄₁N₉O₇S₃.2HCl.2.5H₂O  C   H   N Calcd: 41.38 5.75 14.97 (%) Found: 41.04 5.53 14.96 (%) (B) 1780, 1755, 1680 1620, 1545, 1450 1380 | 0.92, 0.94(3H, each t, J=6Hz), 1.0-2.1 (14H, m), 2.85(6H, s), 3.64(2H, s), 3.66(2H, t, J=6Hz), 3.73&3.93(2H, AB_q, J=18Hz), 4.27& 4.53, 4.33(2H, each AB_q&b.s, J=13Hz), 4.66(1H, b), 4.80 (2H, t, J=6Hz), 5.14, 5.17(1H, each d, J=5Hz), 5.72, 5.76(1H, each d.d, J=5&8Hz), 6.68(1H, s), 6.76, 6.83(1H, each t, J=5Hz), 9.24, 9.28(1H, each d, J=8Hz) |
| 5-8 | —(CH₂)₂CH₃ | (cycloheptyl) | (A) C₃₀H₄₃N₉O₇S₃.2HCl.H₂O  C   H   N Calcd: 43.47 5.72 15.21 (%) Found: 43.42 5.59 15.09 (%) (B) 1780, 1755, 1680 | 0.91, 0.92(3H, each t, J=6Hz), 1.0-2.2 (16H, m), 2.84(6H, s), 3.64(2H, s), 3.64(2H, t, J=6Hz), 3.71&3.91(2H, AB_q, J=18Hz), 4.27& 4.51, 4.32(2H, each |

TABLE 6-continued

Formula:

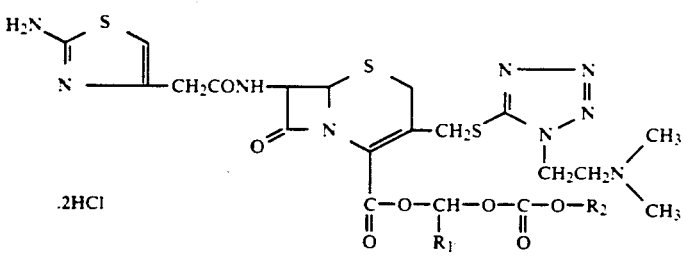
.2HCl

| Example No. | $R_1$ | $R_2$ | (A) Elemental analysis for (B) IR (KBr) (cm$^{-1}$) | NMR (DMSO-d$_6$, δ-value) |
|---|---|---|---|---|
| | | | 1625, 1540, 1460 1380 | AB$_q$&b.s, J=13Hz), 4.0–5.0(1H, b), 4.80(2H, t, J=6Hz), 5.12, 5.15(1H, each d, J=5Hz), 5.71, 5.75(1H, each d.d, J=5&8Hz), 6.67(1H, s), 6.73, 6.81(1H, each t, J=5Hz), 9.21, 9.25(1H, each d, J=8Hz) |
| 5-9 | —(CH$_2$)$_2$CH$_3$ | CH$_3$ ((trans)-2-methylcyclohexyl) | (A) C$_{30}$H$_{43}$N$_9$O$_7$S$_3$.2HCl.1.5H$_2$O C H N Calcd: 43.01 5.77 15.05 (%) Found: 43.18 5.96 15.04 (%) (B) 1780, 1760, 1680 1630, 1540, 1460 1380 | 0.87(3H, d, J=6Hz), 0.90, 0.92(3H, each t, J=6Hz), 1.0–2.2 (13H, m), 2.84(6H, s), 3.64(2H, s), 3.65(2H, t, J=6Hz), 3.72&3.92(2H, AB$_q$, J=18Hz), 4.27& 4.51, 4.32(2H, each AB$_q$&b.s), 4.79 (2H, t, J=6Hz), 4.20(1H, b), 5.13, 5.17(1H, each d, J=5Hz), 5.71, 5.75(1H, each d.d, J=5&8Hz), 6.65 (1H, s), 6.74, 6.83 (1H, each t, J=5Hz), 9.20, 9.24(1H, each d, J=8Hz) |
| 5-10 | —(CH$_2$)$_2$CH$_3$ | ((endo)-3-norbornyl) | (A) C$_{30}$H$_{41}$N$_9$O$_7$S$_3$.2HCl.1.5H$_2$O C H N Calcd: 43.11 5.55 15.08 (%) Found: 42.96 5.76 15.09 (%) (B) 1780, 1760, 1680 1630, 1550, 1530 1455, 1380 | 0.90, 0.92(3H, each t, J=6Hz), 1.0–2.4 (14H, m), 2.84(6H, s), 3.64(2H, s), 3.64(2H, t, J=6Hz), 3.72&3.92(2H, AB$_q$, J=18Hz), 4.26& 4.52, 4.32(2H, each AB$_q$&b.s, J=13Hz), 4.80(2H, t, J=6Hz), 4.0–5.0(1H, b), 5.13, 5.17(1H, each d, J=5Hz), 5.72, 5.77 (1H, each d.d., J= 5&8Hz), 6.65(1H, s), 6.73, 6.83(1H, each t, J=5Hz), 9.21, 9.24 (1H, each d, J=8Hz) |
| 5-11 | —CH(CH$_3$)$_2$ | (cyclopentyl) | (A) C$_{28}$H$_{39}$N$_9$O$_7$S$_3$.2HCl.4.5H$_2$O C H N Calcd: 38.93 5.83 14.59 (%) Found: 38.96 5.55 15.63 (%) (B) 1780, 1750, 1680 1620, 1530, 1460 1380 | 0.96(6H, d, J=7Hz), 1.3–2.4(9H, m), 2.83(6H, s), 3.64 (2H, s), 3.64(2H, t, J=6Hz), 3.72& 3.92(2H, AB$_q$, J=18Hz), 4.26& 4.51, 4.32(2H, each AB$_q$&b.s, J=13Hz), 4.79(2H, t, J=6Hz), 5.02(1H, b), 5.13, 5.17(1H, each d, J=5Hz), 5.72, 5.77 (1H, each d.d, J=5&8 Hz), 6.56, 6.63(1H, each d, J=5Hz), |

TABLE 6-continued

Formula

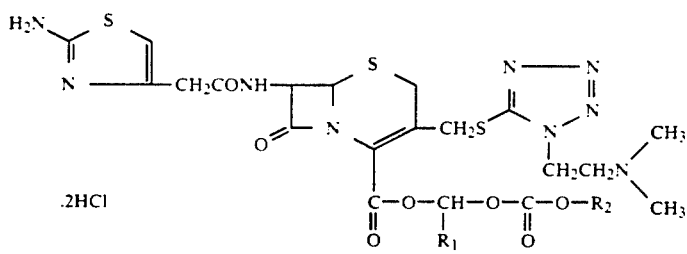

.2HCl

| Example No. | R₁ | R₂ | (A) Elemental analysis for (B) IR (KBr) (cm⁻¹) | NMR (DMSO-d₆, δ-value) |
|---|---|---|---|---|
| 5-12 | —CH(CH₃)₂ | (cyclohexyl) | (A) C₂₉H₄₁N₉O₇S₃·2HCl·3H₂O<br>    C  H  N<br>Calcd: 40.94 5.80 14.82<br>(%)<br>Found: 40.83 5.67 15.10<br>(%)<br>(B) 1780, 1755, 1670<br>1620, 1540, 1450<br>1380 | 6.66(1H, s), 9.22, 9.26(1H, each d, J=8Hz)<br>0.96(6H, d, J=7Hz), 1.0–2.4(11H, m), 2.83(6H, s), 3.64 (2H, s), 3.64(2H, t, J=6Hz), 3.73& 3.92(2H, ABq, J=18Hz), 4.25&4.50, 4.30(2H, each ABq &b.s, J=13Hz), 4.79(2H, t, J=6Hz), 4.0–5.0(1H, b), 5.14, 5.17(1H, d, J=5Hz), 5.73, 5.77(1H, each d.d, J=5&8Hz), 6.58, 6.64(1H, each d, J=5Hz), 6.66(1H, s), 9.21, 9.24(1H, each d, J=8Hz) |
| 5-13 | —CH(CH₃)₂ | (cycloheptyl) | (A) C₃₀H₄₃N₉O₇S₃·2HCl·5H₂O<br>    C  H  N<br>Calcd: 40.00 6.15 13.99<br>(%)<br>Found: 39.82 5.71 13.87<br>(%)<br>(B) 1780, 1750, 1660<br>1620, 1550, 1530<br>1460, 1380 | 0.96(6H, d, J=7Hz), 1.0–2.4(13H, m), 2.84(6H, s), 3.64 (2H, s), 3.64(2H, t, J=6Hz), 3.73& 3.93(2H, ABq, J=18Hz), 4.27&4.50, 4.32(2H, each ABq &b.s, J=13Hz), 4.80(2H, t, J=6Hz), 4.0–5.0(1H, b), 5.14, 5.18(1H, each d, J=5Hz), 5.73, 5.78(1H, each d.d, J=5&8Hz), 6.58, 6.64(1H, each d, J=5Hz), 6.67(1H, s), 9.23, 9.26(1H, each d, J=Hz) |
| 5-14 | —CH(CH₃)₂ | ((trans)-2-methylcyclohexyl) | (A) C₃₀H₄₃N₉O₇S₃·2HCl·2H₂O<br>    C  H  N<br>Calcd: 39.60 6.20 13.85<br>(%)<br>Found: 39.53 5.63 14.61<br>(%)<br>(B) 1780, 1755, 1660<br>1620, 1530, 1460<br>1380 | 0.88(3H, d, J=6Hz), 0.96(6H, d, J=7Hz), 1.0–2.3(10H, m), 2.84(6H, s), 3.64 (2H, s), 3.64(2H, t, J=6Hz), 3.72& 3.92(2H, ABq, J=18Hz), 3.9–4.5(1H, b), 4.27&4.49, 4.31(2H, each ABq &b.s, J=13Hz), 4.79(2H, t, J=6Hz), 5.13, 5.16(1H, each d, J=5Hz), 5.73, 5.77(1H, each d.d, J=5&8Hz), 6.58, 6.64(1H, each d, J=5Hz), 6.66(1H, s), 9.24, 9.26(1H, each d, J=8Hz) |

EXAMPLE 6

(a) Production of 1-(Cyclohexyloxycarbonyloxy)Ethyl 3-[[[1-(2-Dimethylaminoethyl)-1H-Tetrazol-5-Yl]Thio]Methyl]Ceph-3-Em-4-Carboxylate Dihydrochloride To 120 ml of a dimethylformamide solution containing 8.44 g of 7β-amino-3-[[[1-(2-dimethylaminoethyl)-1H-tetrazol-5-yl]thio]methyl]ceph-3-em-4-carboxylic acid dihydrochloride is added 3.34 g of potassium acetate and this solution is cooled to 0° C. With stirring, 10.0 g of 1-iodoethyl cyclohexyl carbonate is added dropwise to said solution, followed by stirring at 0° C. for 5 minutes. The reaction mixture is poured into a mixture of 120 ml of methylene chloride and 120 ml of 0.1N-HCl. The aqueous layer is separated and is adjusted to pH 6.0 with a saturated aqueous sodium bicarbonate solution and extracted with methylene chloride. Water is added to the methylene chloride solution and the aqueous solution is adjusted to pH 2.0 with 4N-HCl. The aqueous layer is separated and remaining methylene chloride is removed therefrom under reduced pressure. Then, the aqueous solution is lyophilized to obtain 5.44 g of the title compound.

IR (Nujol) cm$^{-1}$: 1780, 1750, 1670.

(b) Production of 1-(Cyclohexyloxycarbonyloxy)Ethyl 7β-[2-(2-Aminothiazol-4-Yl)Acetamido]-3-[[[1-(2-Dimethylaminoethyl)-1H-Tetrazol-5-Yl]Thio]Methyl]-Ceph-3-Em-4-Carboxylate Dihydrochloride.

To a mixture of 30 ml of water and 30 ml of methylene chloride is added 1.8 g of the compound obtained in the above (a), to which is added 0.55 g of sodium bicarbonate with stirring. The organic layer is separated and dried over anhydrous calcium chloride. After removal of the drying agent by filtration, is added to the filtrate 20 ml of a dimethylformamide solution containing 0.60 g of (2-aminothiazol-4-yl)acetic acid hydrochloride and 0.62 g of dicyclohexylcarbodiimide, followed by stirring the mixture at room temperature. The resulting precipitate is removed by filtration. To the filtrate are added 150 ml of ethyl acetate and 100 ml of ice-cooled water. The organic layer is separated, washed with water and saturated aqueous sodium chloride and dried over anhydrous magnesium sulfate. After removal of the drying agent by filtration, the filtrate is concentrated to 10 ml under reduced pressure. To the residual solution is added an anhydrous ethereal hydrogen chloride solution, and the resultant precipitate is collected by filtration to obtain 0.26 g of white powder.

This product shows the same NMR and IR spectra as those of the product obtained according to Method A of Example 2-1.

EXAMPLE 7

Production of 1-(Cyclohexyloxycarbonyloxy)Ethyl 7β-[2-(2-Aminothiazol-4-Yl)Acetamido]-3-[[[1-(2-Dimethylaminoethyl)-1H-Tetrazol-5-Yl]Thio]Methyl]-Ceph-3-Em-4-Carboxylate Dihydrochloride To a mixture of 15 ml of water and 15 ml of methylene chloride is added 1.2 g of 1-(cyclohexyloxycarbonyloxy)ethyl 7β-amino-3-[[[1-(2-dimethylaminoethyl)-1H-tetrazol-5-yl]ceph-3-em-4-carboxylate dihydrochloride obtained in Example 6(a). This mixture is stirred together with 0.30 g of sodium bicarbonate. The organic layer is separated and dried over anhydrous calcium chloride, followed by removal of the solvent by distillation under reduced pressure. The residue is dissolved in 15 ml of methylene chloride and cooled to −25° C. To this solution is added a solution of 0.5 g of 4-chloroacetoacetyl chloride in 2.0 ml of methylene chloride. The mixture is stirred at −20° C.-−15° C. for 20 minutes and then 0.76 g of thiourea and 5 ml of dimethylacetamide are added thereto. The mixture is stirred at room temperature for 3 hours. Water is added to the reaction mixture and the aqueous layer is separated, adjusted to pH 6.0 and extracted with methylene chloride. The methylene chloride solution is admixed with water and adjusted to pH 1.5 with 2N-HCl. The aqueous layer is separated and remaining methylene chloride is distilled off under reduced pressure. Then, the aqueous solution is subjected to column chromatography on Diaion CHP-20P (75-150 μ, Mitsubishi Chemical Industries, Ltd., Japan), elution being carried out with 120 ml of 0.01N-HCl and then 20% acetonitrile-0.01N-HCl. The eluate is lyophilized to obtain 0.37 g of white powder. This product shows the same NMR and IR spectra as those of the product obtained according to Method A of Example 2-1.

EXAMPLE 8

(a) Production of 1-(Cyclohexyloxycarbonyloxy)Ethyl 7β-[2-(2-Aminothiazol-4-Yl)Acetamido]-3-Acetoacetoxymethylceph-3-Em-4-Carboxylate In 30 ml of N,N-dimethylformamide is dissolved 4.76 g of sodium 7β-[2-(2-aminothiazol-4-yl)acetamido]-3-acetoacetoxymethylceph-3-em-4-carboxylate and the solution is cooled to −5° C. With stirring, to the solution is added dropwise 5.0 g of 1-iodoethyl cyclohexyl carbonate, followed by stirring for further 5 minutes. The reaction mixture is poured into a mixture of 300 ml of ethyl acetate and 200 ml of ice water and the organic layer is separated. The aqueous layer is extracted with 200 ml of ethyl acetate. The organic layers are combined and washed with 150 ml each portion of ice water (three times) and saturated aqueous sodium chloride (three times) and then dried over anhydrous magnesium sulfate. The solution is then distilled off under reduced pressure and isopropyl ether is added to the residue. The resultant white powder is collected by filtration, washed with isopropyl ether and dried to obtain 3.3 g of the title compound.

IR (KBr) cm$^{-}$: 1780, 1750, 1680.

NMR (DMSO-d6 90 MHz) δ: 1.52, 1.55 (3H, each d, J=6 Hz), 1.0-2.2 (10H, m), 2.10 (3H, s), 3.50 (2H, b.s), 3.60 and 3.85 (2H, ABq, J=18 Hz), 4.03 and 4.20 (2H, ABq, J=13 Hz), 5.01 (1H, d, J=5 Hz), 5.6-5.8 (1H, m), 6.25 (1H, s), 6.6-7.2 (3H, m), 8.89 (1H, d, J=8 Hz).

(b) Production of 1-(Cyclohexyloxycarbonyloxy)Ethyl 7β-[2-(2-Aminothiazol-4-Yl)Acetamido-3-[[[1-(2-Dimethylaminoethyl)-1H-Tetrazol-5-Yl]Thio]Methyl]Ceph-3-Em-4-Carboxylate Dihydrochloride To 30 ml of an acetone solution containing 2.3 g of the compound obtained in the above (a) is added 10 ml of an aqueous solution containing 0.8 g of sodium bicarbonate and 0.9 g of 1-(2-dimethylaminoethyl)-5-mercapto-1H-tetrazole. The mixture is heated at 40° C. for 1 hour with stirring. The reaction mixture is poured into a mixture of 150 ml of ethyl acetate and 50 ml of ice water and the organic layer is separated, washed with ice water and then with saturated aqueous sodium chloride. This is then dried over anhydrous magnesium sulfate and thereafter the solvent is distilled off under reduced pressure The residue is dissolved in 20 ml of 0.1N-HCl and subjected to column chromatography on Diaion CHP-20P (75-150 μ, Mitsubishi Chemical Industries, Ltd., Japan), elution being carried out with 0.01N-HCl and then with 20% acetonitrile-0.01N-HCl. The eluate is lyophilized to obtain 0.04 g of white powder which is the title compound.

This product shows the same NMR and IR spectra as those of the product obtained according to Method A of Example 2-1.

FORMULATION EXAMPLE 1

1-(Cyclohexyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (382.8 g; 250 g in terms of the non-ester, i.e. compound[II]) as obtained in Example 2-1 is evenly admixed with 70.5 g of hydroxypropylcellulose and 70.5 g of carboxymethylcellulose and the mixture is distributed in 261.9 mg portions (125 mg in terms of the non-ester) into capsules in the conventional manner.

FORMULATION EXAMPLE 2

1-(Cyclohexyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (382.8 g; 250 g in terms of the non-ester, i.e. compound [II]) as obtained in Example 2-1 is evenly admixed with 70 g of starch and 6 g of hydroxypropylcellulose and the mixture is tableted in the conventional manner to provide 229.4 mg tablets (125 mg in terms of the non-ester).

EXPERIMENTAL EXAMPLE

The compounds of Examples 1-1, 1-5, 1-6, 2-1, 2-10, 2-11, 2-12, 2-13, 5-2, 5-7 and, as a control compound, the 1-(ethoxycarbonyloxy)ethyl ester of compound [II], i.e. 1-(ethoxycarbonyloxy)ethyl 7β-[2-(2-aminothiazol-4-yl)acetamido]-3-[[[1-(2-dimethylaminoethyl)-1H-tetrazol-5-yl]-thio]methyl]ceph-3-em-4-carboxylate (hereinafter referred to as compound A) are administered orally to mice, each compound to one animal, in the dose of 100 mg/kg (in terms of non-ester form thereof, i.e. compound [II]). At 0.25, 0.5, 1.0 and 2.0 hours after administration, the concentration of compound [II] in plasma of the mouse is measured by the cup method using *Proteus mirabilis* Eb 313 as the test organism and the area under plasma concentration-time curve from zero to 2 hours (AUC) is calculated.

CONTROL TEST

The compound [II] was subcutaneously applied and AUC was calculated in the same manner as above.

The bioavailability defined in the following formula is shown in the Table 7.

Bioavailability (%) =

-continued $$\frac{AUC \text{ (oral administration)}}{AUC \text{ (subcutaneous administration)}} \times 100$$

TABLE 7

| Example No. | Plasma level of non-ester compound (compound [II]) (μg/ml), n = 4* | | | | AUC (μg · hr/ml) | Bioavailability (%) |
|---|---|---|---|---|---|---|
| | 0.25 | 0.5 | 1 | 2(hr) | | |
| 1-1 | 28.2 | 26.0 | 16.4 | 1.7 | 30.0 | 77.2 |
| 1-5 | 14.2 | 29.2 | 23.6 | 1.8 | 33.1 | 85.3 |
| 1-6 | 25.5 | 34.3 | 12.6 | 1.5 | 29.4 | 75.9 |
| 2-1 | 39.7 | 34.5 | 8.9 | 0.9 | 30.0 | 77.1 |
| 2-10 | 34.2 | 32.5 | 11.3 | 1.7 | 30.1 | 77.4 |
| 2-11 | 35.3 | 29.1 | 14.9 | 1.5 | 35.4 | 91.2 |
| 2-12 | 55.1 | 34.3 | 11.5 | 0.6 | 35.5 | 91.5 |
| 2-13 | 52.4 | 32.6 | 12.6 | 2.6 | 36.1 | 93.0 |
| 5-2 | 49.7 | 38.0 | 5.8 | 0.6 | 31.3 | 80.7 |
| 5-7 | 51.7 | 44.9 | 7.9 | 1.1 | 36.3 | 93.5 |
| Compound A Control: | 14.7 | 9.2 | 2.4 | 0.7 | 9.28 | 23.9 |
| subcutaneous administration of compound[II] | 69.2 | 29.0 | 13.2 | 1.5 | 38.8 | 100 |

*Average for 4 mice

We claim:

1. 1-(cyclohexyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate, or a pharmaceutically acceptable salt thereof.

2. A compound according to claim 1, wherein the pharmaceutically acceptable salt is dihydrochloride.

3. An antibiotic composition comprising a pharmaceutically effective amount of 1-(Cyclohexyloxycarbonyloxy)ethyl 7β-[2-(2-amino-thiazol-4-yl)acetamido]-3-[[[1-(2-dimethylaminoethyl)-1H-tetrazol-5-yl]thio]methyl]ceph-3-em-4-carboxylate, or a pharmaceutically acceptable salt thereof as an effective ingredient in combination with a pharmaceutically acceptable carrier.

4. A pharmaceutical composition according to claim 3, wherein the pharmaceutically acceptable salt is dihydrochloride.

5. An antibiotic composition comprising a pharmaceutically effective amount of 1-(Cyclohexyloxycarbonyloxy)ethyl 7β-[2-(2-amino-thiazol-4-yl)acetamido]-3-[[[1-(2-dimethylaminoethyl)-1H-tetrazol-5-yl]thio]methyl]ceph-3-em-4-carboxylate, or a pharmaceutically acceptable salt thereof as an effective ingredient in combination with a pharmaceutically acceptable carrier other than a cyclodextrin.

* * * * *